United States Patent
Duda et al.

(10) Patent No.: US 11,639,935 B2
(45) Date of Patent: May 2, 2023

(54) CD8+T-CELL SUBSETS AS MARKERS FOR PREDICTION OF DELAYED FRACTURE HEALING

(71) Applicant: Charite Universitätsmedizin Berlin, Berlin (DE)

(72) Inventors: Georg Duda, Berlin (DE); Hans-Dieter Volk, Berlin (DE); Simon Reinke, Berlin (DE); Christian Meisel, Berlin (DE); Christian Kleber, Berlin (DE); Sven Geissler, Berlin (DE); Katharina Schmidt-Bleek, Berlin (DE)

(73) Assignee: CHARITÉ UNIVERSITATSMEDIZIN BERLIN, Berlin (DE)

( * ) Notice: Subject to any disclaimer, the term of this patent is extended or adjusted under 35 U.S.C. 154(b) by 409 days.

(21) Appl. No.: 16/711,480

(22) Filed: Dec. 12, 2019

(65) Prior Publication Data
US 2020/0116721 A1 Apr. 16, 2020

Related U.S. Application Data

(63) Continuation of application No. 14/376,398, filed as application No. PCT/EP2013/052181 on Feb. 4, 2013, now abandoned.

(30) Foreign Application Priority Data

Feb. 3, 2012 (EP) .................................... 12153850

(51) Int. Cl.
*G01N 33/569* (2006.01)
*A61K 31/00* (2006.01)
*A61K 39/395* (2006.01)

(52) U.S. Cl.
CPC ....... *G01N 33/56966* (2013.01); *A61K 31/00* (2013.01); *A61K 39/395* (2013.01); *G01N 33/56972* (2013.01); *G01N 2333/70517* (2013.01); *G01N 2333/70596* (2013.01); *G01N 2800/10* (2013.01); *G01N 2800/52* (2013.01)

(58) Field of Classification Search
CPC ....... G01N 33/56966; G01N 33/56972; G01N 2333/70517; G01N 2333/70596; G01N 2800/10; G01N 2800/52; G01N 2015/1037; G01N 2015/1081; A61K 31/00; A61K 39/395; C07K 2317/76; C07K 2317/70; C07K 16/241; C07K 16/249; A61P 19/00
See application file for complete search history.

(56) References Cited

U.S. PATENT DOCUMENTS

| 6,180,403 | B1 | 1/2001 | Flournoy et al. |
|---|---|---|---|
| 2003/0129665 | A1 | 7/2003 | Selvan et al. |
| 2007/0166307 | A1 | 7/2007 | Bushell et al. |
| 2012/0014947 | A1 | 1/2012 | Fu et al. |

FOREIGN PATENT DOCUMENTS

| CN | 1717177 | 1/2006 |
|---|---|---|
| JP | 2003512068 | 4/2003 |
| JP | 2007089788 | 4/2007 |
| JP | 2008515819 | 5/2008 |
| JP | 2008536826 | 9/2008 |
| JP | 2009511600 | 3/2009 |
| JP | 2011517672 | 6/2011 |
| JP | 2013511708 | 4/2013 |
| WO | 2002024228 | 3/2002 |
| WO | 03/067210 | 8/2003 |
| WO | 2006/100033 | 9/2006 |

OTHER PUBLICATIONS

Volk, Hans Dieter et al.: "Mulitparameteranalytic von Immunzellen", BCRT-Berlin-Brandenburg Center for Regenerative Therapies, Mar. 16, 2012.
Andrews R G et al.: "Differential engraftment of genetically modified CD34 <+> andCD34<-> hematopoietic cell subsets in lethal irradiated baboons", Experimental Hematology, vol. 28, No. 5, 2000, pp. 508-518.
Schmidt-Bleek Katharina et al.: "inflammatory phase of bone healing initiates the regenerative healing cascade" Cell and Tissue Reseach, vol. 347, No. 3, Mar. 2012, pp. 567-573.
Coulibaly Marlon O et al.: "Recent advances in the use of serological bone formation makers to monitor callus development and fracture healing", PubMed Central (PMC) Author Manuscript Critical Reviews in Eukaryotic Gene Expression, vol. 20, No. 2, 2010, pp. 1-26.
Strioga etal (Immunology,2011, 134,17-32).
Calori et al. (Injury Int J. Care Injured 2008, 39S2 S59-S63).
Wu et al. (Clin Cancer Res, published on line Feb. 3, 2012, 18(9) 2465-2477).
BD Facsariaii user guide retrieved from https://www.bdbiosciences.com/documents/BD FACSAria II User Guide.pdf.
Benoist et al., Science 2011, vol. 332 p. 667-668.
BD FACService Technote (Customer Focused Solutions vol. 9 No. Oct. 4, 2004 retireved from https://www.bdbiosciences.com/documents/BD Research_Sorting_TechBulletin.pdf).
Brenchley et al. (Blood 2003;vol. 1 No. 7,p. 2717.
"CD4+ T cell and CD8+ T cell" The Intestinal Microbiology Society / Formerly Japan Bifidus Foundation's URL: https://bifidus-fund.jp/keyword/kw045.shtml.

(Continued)

*Primary Examiner* — Carmencita M Belei
(74) *Attorney, Agent, or Firm* — JMB Davis Ben-David

(57) ABSTRACT

The present invention relates to a method for diagnosis of delayed bone fracture healing, comprising determining the frequency of a subpopulation of CD8+ cells selected from a first group comprised of CD8+CD57+, CD8+CD28− and CD8+CD28−/CD57+, in a sample obtained from a subject. The present invention further relates to a system and a kit of parts for prediction and resulting options for preventing of delayed bone fracture healing.

2 Claims, 16 Drawing Sheets

(56) References Cited

OTHER PUBLICATIONS

Moghaddam et al. "Clinical application of BMP 7 in long bone non-unions" Archives of Orthopaedic and Trauma Surgery(Including Arthroscopy and Sports Medicine),vol. 130, No. 1, Nov. 3, 2009, pp. 71-76 (abstract and selected pages provided).
Gulotta et al. "TNF-alpha Blockade Improves Early Tendon-to-Bone Healing in a Rat Rotator Cuff Repair Model" Arthroscopy. The Journal of Arthroscopic and Related Surgery"Article: (SS-10)", Raven Press, New York, NY, US, vol. 25, No. 6, Jun. 1, 2009,pages e5-e6.
Vignery et al., "Recombinant Murine Interferon-gamma Inhibits the Fusion of Mouse Alveolar Macrophages In Vitro but Stimulates the Formation of Osteoclastlike Cells on Implanted Syngeneic Bone Particles in Mice In Vivo", Journal of Bone and Mineral Research vol. 5, Jun. 1, 1990 (p. 637-644).
Malviya, "The effect of newer anti-rheumatic drugs on osteogenic cell proliferation: an in-vitro study", Journal of Orthopaedic Surgery and Research, vol. 4, No. 1, May 26, 2009 p. 17.
Sandberg, "Etanercept does not impair healing in rat models of tendon or metaphyseal bone injury," ACTA Orthopaedica, vol. 83, No. 3, May 23, 2012, pp. 305-310.
Pradilla, "Prevention of vasospasm following Subarachnoid hemorrhage in rabbits by anti-CD/CD18 monoclonal antibody therapy" Journal of Neurosur, vol. 101, Jul. 1, 2004, pp. 88-92.
Reinke, "Terminally Differentiated CD8+ T Cells Negatively Affect Bone Regeneration in Humans" Science Translation Medicine, vol. 5, No. 177, Mar. 20, 2013.

CD8+T-CELL SUBSETS AS MARKERS FOR PREDICTION OF DELAYED FRACTURE HEALING

CROSS-REFERENCE TO RELATED APPLICATIONS

This is a Continuation of U.S. patent application Ser. No. 14/376,398, filed Aug. 1, 2014, which is the National Stage entry of International Patent Application No. PCT/EP2013/052181, filed Feb. 4, 2013, which in turn claimed the benefit of European Patent Application No. 12153850.8, filed Feb. 3, 2012. The contents of the foregoing patent applications are incorporated by reference herein in their entirety.

FIELD

The present invention relates to a method, a system and a kit for prediction and prevention of delayed bone fracture healing.

BACKGROUND

Fracture healing is a physiological process with sequential, overlapping stages and results in a restoration of bone tissue. Under certain risk factors, however, such as severe fractures, old age, steroid therapy or diabetes, this process can be delayed or even incomplete (non-union healing) with poor long-term outcome and a high socio-economic impact. Delayed or incomplete healing can be observed in approximately 5-10% of patients following a fracture of the long bones.

Only limited knowledge is available about the mechanisms behind poor healing. There is growing evidence suggesting a key role of inflammation and T-cell response within the bone repair processes following injury, wherein the T-cell response affects processes such as chemotaxis, recruitment of further immune and mesenchymal cells resulting in stimulating angiogenesis, and finally, enhancement of extracellular matrix synthesis (Schmidt-Bleek et al., J Orthop Res.; 27(9):1147-51; Kolar et al., Tissue Eng Part B Rev.; 16(4):427-34; Toben et al. J Bone Miner Res., January; 26(1):113-24).

Recent data show that mice deficient for adaptive immunity surprisingly expressed enhance bone healing although the mineralisation was less effective than in controls (Colburn et al. Arthritis Rheum.; 60(6):1694-703; Schmidt-Bleek et al. Cell Tissue Res; DOI 10.1007/s00441-011-1205-7). Furthermore, a significantly higher cytotoxic T cell percentage within hematoma was found in sheep with delayed/impaired healing, due to a treatment with a mechanically critical external fixator having a high rotational instability, compared with rigidly fixated animals.

Osteocalcin and bone alkaline phosphatase have been investigated as predictive markers for delayed fracture healing. Only osteocalcin, however, showed minor differences between patients with normal and delayed fracture healing, and not before forty-two days after the fracture occurred. Furthermore, transforming growth factor beta 1 (TGF-beta 1) has been discussed as another potential biomarker. Examinations showed that after 4 weeks post fracture TGF-beta 1 levels of patients with delayed bone fracture healing were lower than the levels of patients showing normal healing. However, these parameters have only a limited validity for the prediction of bone healing due to a high intra-inter patients variability, a short half life of the cytokines, and a late predictive time point during the fracture healing.

There is an unmet need for biomarkers predicting the outcome after bone fracture to administer supporting therapies as early as possible, such as growth factors like BMP (bone morphogenetic protein), which are costly and not free of adverse effects.

The objective of the instant invention is to provide means and methods for the prediction of delayed bone fracture.

SUMMARY

The present invention was made during the course of an investigation assessing the inflammatory reaction and immune cell composition in peripheral blood of proximal tibial fracture patients during the healing process at typical time points of clinical relevance. Relevant differences in the immune cell composition in the peripheral blood during the fracture healing process related to a delayed healing were identified.

Total T-cell counts (CD3+) or the major subset distribution (CD3+4+ and CD3+8+) did not show differences between the groups (normal vs. delayed healing). However, it was surprisingly found that delayed healing was strongly associated with a significantly enhanced frequency of terminally differentiated CD8+ effector T cells expressing the phenotype CD8+11a++28− and/or CD8+11a++57+ and/or CD8+11a++CD28−57+, which corresponds to CD8+ TEMRA cells (CD57+8+ delayed healing vs. normal: 1.6-1.8 fold, CD28−8+ delayed healing vs. normal: 1.5-1.6 fold; CD11++8+ delayed healing vs. normal: 1.2-1.3 fold) at different time points post injury/operation (<1 wk to >18 wk). CD8+ TEMRA cells also express the marker phenotype CCR7−CD45RA+CD45RO−. This difference was stable over follow-up time of 18 weeks reflecting rather the individual immune experience than the post-trauma reaction to the fracture.

CD8+ TEMRA cells are characterized by their (inflammatory) tissue homing properties and strong bystander responsiveness. They can be also triggered independently of their T-cell receptor (TCR) in an antigen-independent matter by cytokines, such as IL-6, IL-8, IL-12, IL-18, IL-23, or TNFα. Those cytokines are delivered by cells of the innate immune system triggered in the fracture hematoma as a result of interaction between toll-like receptor molecules (TLR) and damage-associated molecular patterns (DAMPs). Furthermore, macrophages and dendritic cells can trigger the release of inflammatory cytokines (e.g. IFN-gamma) by these CD8+ TEMRA cells, which support overwhelming inflammation and fibrosis as well as inhibition of osteogenesis. Additionally, these cells are up-regulated in chronic immune activation states, such as in infectious diseases, like HIV, tuberculosis or cytomegalovirus.

Another surprising finding was that the frequency of another small subset of CD3+ T cells in the peripheral blood, the so-called double positive CD4+8+ T cells, is also enhanced in delayed healing patients.

BRIEF DESCRIPTION OF THE FIGURES

FIG. 7B: IL-8) of in blood samples of normal and delayed healing patients (median, lower and upper quartiles).

FIG. 10E: BM-MSC apoptosis rate following cytokine exposure. BM-MSCs vitality determined with alamarBlue® after culture in media supplemented with indicated cytokine concentrations (FIGS. 10F-10H).

FIG. 11C shows a progressive increase in CD8+ T cells in BM from the CD8− group, WT group, WTexp group, to the highest percentages detected in the CD8+ group. Similar results were found for the memory CD62L-CD8+ T cell subpopulation, which were also significantly lower in the CD8− group compared to all other groups (FIG. 11B). μCT evaluation of the fracture callus quality showed a progressive decrease in the bone volume to total volume ratio (BV/TV) and bone volume density from CD8− group to the CD8+ group (FIG. 11D-H).

DETAILED DESCRIPTION

According to a first aspect of the invention, an ex vivo method for prognosis of delayed bone fracture healing is provided, comprising determining the frequency of a subpopulation of CD8+ T cells selected from a first group comprised of CD8+CD57+ cells, CD8+CD28− cells and/or CD8+CD28−CD57+ cells, in a sample obtained from a subject.

According to an alternative of this first aspect of the invention, an ex vivo method for prognosis of delayed bone fracture healing is provided, comprising determining the frequency of a subpopulation of CD8+ T cells selected from a first group comprised of CD8+CD11a+CD57+ cells, CD8+CD11a+CD28− cells and/or CD8+CD11a+CD28−CD57+ cells, in a sample obtained from a subject.

In some embodiments, the sample is a blood sample, in particular obtained from peripheral blood, or a biopsy sample obtained from a region in the vicinity of a bone fracture, in particular from the inflammatory peri-fracture hematoma.

In some embodiments, the method of the invention is used for predicting the outcome after bone fracture or for classifying a sample from a subject, wherein the sample is assigned to a probability of an outcome after bone fracture.

Frequency in the sense of the invention refers to the number of cells defined by certain marker molecules presented on the surface of these cells in relation to the number of cells of an entire definable population. For example, a frequency of 5% for the CD8+CD4+ subpopulation of the CD3+ cells means that 5% of all CD3+ cells belong to the CD8+CD4+ subpopulation.

In some instances, cells may be characterized herein by showing the cluster of differentiation positivity/negativity in abbreviated form: CD4+8+ is synonymous with CD4+CD8+.

Generally, for the methods disclosed herein, the frequency of a given subpopulation is determined in relation to the total number of the parent population (as indicated in each table CD3+ or CD8+ cells, respectively) in the sample.

Figure 12:
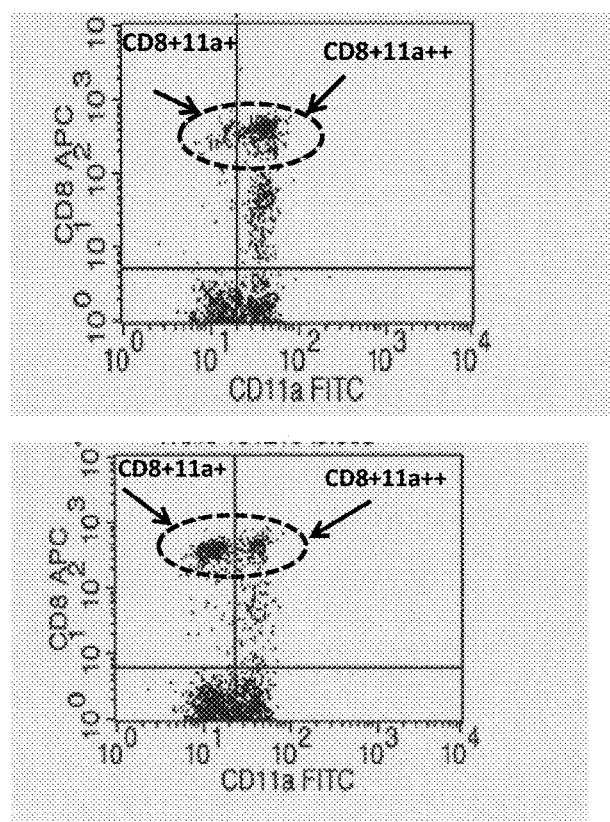
FIG. 12 show two examples (top and bottom panels) for determination of CD11a++ cells.

If any cell population is designated "positive" with respect to a certain marker molecule herein, this designation shall mean that said cell population can be stained by a common fluorescent-dye-labeled antibody against the marker molecule and will give a fluorescence signal of at least one, two or three log higher intensity compared to unlabeled cells or cells labeled with the same antibody but commonly known as not expressing said marker molecule or an isotype control antibody. Vice versa, any cell population that is designated "negative" with respect to certain marker molecule cannot be stained by a fluorescent-dye-labeled antibody as described above against the marker molecule. Cells designated "double positive" or "++" with respect to a certain marker molecule means cells exhibiting a high expression of this certain marker molecule which can be separated as a distinct subpopulation by electronic gating. "++" cells give a fluorescence signal significantly stronger than that given by cells at the lower end of the single positive "+" gate. "++" events can typically be distinguished as a distinct cluster. Cells double positive "++" for a given marker are part of the positive "+" population for that marker. FIG. 12 shows a histogram of CD8/CD11 positive and double positive cells: of all CD11a positive cells encircled in the two example histograms, those on the right of the vertical bar constitute the "++" population. In some embodiments, the method of the invention comprises determining the frequency of subpopulation selected from a second group comprised of CD8+CD11a++, CD8+CD11a++CD28−, CD8+CD11a++CD57+, and CD8+CD11a++CD28−CD57+ T cells. In some embodiments, the method according to the above aspect and embodiments of the invention further comprises determining the frequency of a CD8+/CD4+ subpopulation of CD3+ cells.

The predictive or diagnostic value of the method of the invention may be augmented by determining the frequency of additional subpopulations as described above. The frequencies of the additional subpopulations may be determined consecutively or simultaneously. A simultaneous determination is preferred.

In some embodiments, the method further comprises determining the level of IL-6 in the peripheral blood. Thus, the predictive value of the method according to the above aspect and embodiments may further be enhanced by determination of IL-6 as an immunological marker of systemic inflammation. According to the above embodiment, the level may be expressed as a concentration and measured in units such as pg/ml or mol/l.

In some embodiments, the method according to the invention is performed by contacting a sample with a first ligand specifically reactive to a marker molecule selected from a marker group comprised of CD4 (Uniprot ID P01730), CD11a (Uniprot ID P20701), CD28 (Uniprot ID P10747), CD57 and IL-6 (Uniprot ID P05231), and determining the frequency of a cell presenting the marker molecule marked with the first ligand or determining the frequency of the first ligand bound to the marker molecule.

In some embodiments, the first ligand is selected from the group comprised of an antibody, an antibody fragment, an antibody-like-molecule, an oligopeptide of 6 to 30 amino acids, and a nucleic acid aptamer molecule of 10 to 75 nucleotides in length, wherein the ligand is capable to bind to a member of the marker group described in the preceding paragraph with a dissociation constant of $10^{-8}$ mol/l or smaller.

In some embodiments, the antibody fragment is the Fab domain of an antibody (the antigen binding region of an antibody) or a single chain antibody (scFv), a fusion protein consisting of the variable regions of light and heavy chains of an antibody connected by a peptide linker. An antibody fragment or an antibody-like molecule may be manufactured by suitable methods such as recombinant protein expression.

A first ligand may also be developed by evolutive methods such as phage display, ribosome display or SELEX, wherein polypeptides or oligonucleotides are selected according to their binding affinity to a target of interest. Additionally, higher affinity inhibitors may be identified by reiterative rounds of evolution and selection of the amino acid sequence or nucleotide sequence.

In some embodiments, the oligopeptide of 6 to 30 amino acids as referred to above is a peptide derived from the part of a ligand, which is recognized by a member of the marker group described above.

In some embodiments, the ligand that is recognized by a member of the marker group described above is selected from CD80 (Uniprot ID P33681) or CD86 (Uniprot ID P42081), which are ligands of CD28, or CD54 (Uniprot ID P05362), which is a CD11a ligand.

In some embodiments, the first ligand is an antibody reactive to CD4, CD11a, CD28, CD57 and further comprises a fluorescent moiety for optical detection, wherein a marker molecule according to the preceding paragraphs is bound to such antibody, and cells presenting that marker molecule can be counted by a fluorescence based flow cytometric method such as fluorescence activated cell sorting.

In some embodiments, the first ligand is an antibody reactive to IL-6 and may comprise an enzymatic activity, wherein this enzymatic activity is the catalysis of a reaction that can be spectroscopically observed.

In some embodiments, the first ligand is specifically bound by a second ligand, wherein the second ligand comprises an enzymatic activity or a fluorescent moiety.

A plurality of different marker molecules may be determined by use of a plurality of different first ligands, wherein each ligand specifically binds to a particular marker molecule.

In some embodiments, each first ligand of the plurality comprises a certain enzymatic activity or fluorescent moiety as described above that can be spectroscopically distinguished form the enzymatic activity or fluorescent moiety of each other first ligand of the plurality.

In some embodiments, each first ligand is bound be a specific second ligand having a certain enzymatic activity or fluorescent moiety that can be spectroscopically distinguished for the enzymatic activity or fluorescent moiety of each other second ligand.

In some embodiments, the first and second ligand or pluralities thereof are antibodies and used in an Enzyme-linked immunosorbent assay.

In one embodiment, the frequency of a subpopulation according to the preceding aspect of the invention is determined by counting cells that are marked with a fluorescent antibody directed to a marker molecule selected from group comprised of CD4, CD8, CD11a, CD28 and CD57 in a flow cytometric assay.

In one embodiment, the method further comprises determining the Calori-Score of the subject according to the above aspect of the invention.

The Calori-Score in the sense of the invention is a measure for nonunion, the permanent failure of healing following fracture, and may be determined by a method that assesses relevant fracture healing factors such as quality of bone, bone alignment, invasiveness of primary intervention or clinical infection status. A subject showing a Calori-Score that is at least 5% higher than a standard is assigned to a group having an elevated probability for delayed fracture healing. A detailed description of this method can be found in Calori et al., Injury, 39, Supp 2, S59-63, 2008.

In one embodiment, the method further comprises comparing the determined frequency, level or Calori-Score to a standard.

A standard in the sense of the invention means a sample of a subject showing a normal or not delayed bone fracture healing. Alternatively, the standard may be a subject showing a normal bone fracture healing. In particular, fracture healing of a subject is considered normal if none of the following criteria are true:
  i) an incomplete fracture healing after 12 post operative weeks based on the callus formation,
  ii) an incomplete fracture healing after 12 post operative weeks with a fracture gap of larger than 1 mm,
  iii) the presence of a resorption zone or incomplete callus formation,
  iv) an incomplete bridging, which means one to three cortices are bridged,
  v) no bridging, which means no cortex is bridged.

According to a preferred embodiment, a sample exhibiting a twofold higher frequency of CD8+/CD4+ cells compared to a standard determined (retrospectively) for number of patients showing normal fracture healing, is assigned to a group having an elevated probability for delayed fracture healing.

In some embodiments, a sample showing a frequency of T cells being CD11a++, CD28− or CD57+ that is at least 10% higher compared to a standard determined (retrospectively) for number of patients showing normal fracture healing, is assigned to a group having an elevated probability for delayed fracture healing.

In some embodiments, a sample showing a frequency of at least 30% for cells being CD28− or CD57+ of the CD8+ T cells is assigned to a group having an elevated probability for delayed fracture healing, a sample showing a frequency of at least 65% for cells being CD11a++ of the CD8+ T cells is assigned to a group having an elevated probability for delayed fracture healing, and a sample showing a frequency of at least 5% for cells being CD4+ of the CD8+ T cells is assigned to a group having an elevated probability for delayed fracture healing.

In some embodiments, the method of the invention further comprises determining the frequency of a subpopulation of CD4+ T cells, wherein that subpopulation is selected from CD4+CD57+ cells and CD4+CD28− cells.

According to another aspect of the invention, a system for diagnosis of delayed bone fracture healing is provided, comprising
  a device for determination the frequency of a cell population or IL-6 in a sample from a subject, and
  a programmed microprocessor,
  wherein the programmed microprocessor is equipped and designated to run a method according to the above aspects and embodiments of the invention.

In some embodiments, the device is a flow cytometer, comprising a flow cell for transporting and aligning cells, a light source such as a laser and a detector suitable for measuring light or other biophysical parameters such as impedance. Such device may be used for determining the frequency of subpopulations of CD8+ cells according to the above aspects and embodiments of the invention.

In some embodiments, the device may is spectrophotometer or a plate reader, comprising a compartment holding the sample such as a cuvette or a microtiter plate, a light source and a UV/Vis detector suitable for measurement of absorbance or fluorescence, such as a diode array.

In some embodiments, the device is used for determining the level of IL-6 according to the above aspects or embodiments of the invention.

In some embodiments, the programmed microprocessor is integrated in the device described in the preceding paragraphs or is part of a control unit or a computer for operating the device.

In some embodiments, the device described above is equipped and designated to determine the frequency of the subpopulation of CD8+ T cells according to the above aspects and embodiments of the invention.

According to another aspect of the invention, a kit of parts for diagnosis of delayed bone fracture healing is provided, comprising an anti-CD8-antibody, an anti-CD4-antibody, an anti-CD11a-antibody and an anti-CD28-antibody, wherein the above described antibodies are suitable for fluorescence based flow cytometry.

In one embodiment, the kit further comprises an anti-CD57-antibody.

In some embodiments, the antibodies according to the above aspect of the invention are monoclonal antibodies of murine origin and comprise a fluorescent moiety for optical detection in the flow cytometry such as APC (allophycocyanin), FITC (fluorescein isothiocyanate) or PE (phycoerythrin).

In some embodiments, the antibody is selected from the group comprised of PE-Cy7 conjugated mouse anti-human CD4 IgG$_1$, a murine monoclonal antibody conjugated with a PE-Cy7(cyanine dye) tandem fluorophor, APC-Cy7-labelled mouse anti-human CD8 IgG$_1$, a murine monoclonal antibody conjugated with the tandem fluorophor APC-Cy7, FITC-labelled mouse anti-human CD57 IgM, a murine monoclonal antibody, APC-H7 mouse anti-human CD28 IgG$_1$, a murine monoclonal antibody conjugated with the tandem fluorophor APC-H7 being an analogue of APC-Cy7 and having the same spectroscopic properties, and FITC-labelled mouse anti-human CD11a (Anti-LFA-1α, leukocyte function associated antigen-1, alpha polypeptide) IgG$_{2a}$, a murine monoclonal antibody.

According to another aspect of the invention, an inhibitor of IFN-gamma (Uniprot P01579) or TNF-α (Uniprot P01375) is provided for use in a method for treatment of delayed fracture healing, wherein the inhibitor is a ligand to IFN-gamma or TNF-α selected from the group comprised of an antibody, an antibody fragment, an antibody-like-molecule, a soluble receptor construct, an oligopeptide of 6 to 30 amino acids, and a nucleic acid aptamer molecule of 10 to 75 nucleotides in length, an inhibitor of IFN-γ or TNF-α secretion (e.g. si-RNA or small molecules, such as—for example—calcineurin inhibitors) and wherein the ligand (the inhibitor) is capable to selectively bind to IFN-gamma or TNF-α with a dissociation constant of $10^{-8}$ mol/l or smaller, and wherein the ligand to IFN-gamma or TNF-α (the inhibitor) is furthermore capable of abrogating or suppressing the biological effects of IFN-gamma or TNF-α.

In some embodiments of this aspect of the invention, the inhibitor is a monoclonal antibody raised against IFN-gamma or TNF-α. In one embodiment, the inhibitor is a chimeric, humanized, or human monoclonal antibody against IFN-gamma or TNF-α.

In some embodiments of this aspect of the invention, in which the inhibitor is an antibody fragment, the inhibitor is the Fab domain of an antibody (the antigen binding region of an antibody) raised against IFN-gamma or TNF-α, or a single chain antibody (scFv), i.e. a fusion protein consisting of the variable regions of light and heavy chains of an antibody connected by a peptide linker. An antibody fragment or an antibody-like molecule may be manufactured by suitable methods such as recombinant protein expression.

In one embodiment, the inhibitor is a chimeric construct linking an antigen binding-domain selectively binding to IFN-gamma or TNF-α, to the Fc-domain of a human immunoglobulin. One example of such construct is the drug etanercept (CAS No. 185243-69-0).

An inhibitor according to this aspect of the invention may also be developed by evolutive methods such as phage display, ribosome display or SELEX, wherein polypeptides or oligonucleotides are selected according to their binding affinity to IFN-gamma or TNF-α. In some embodiments, the oligopeptide of 6 to 30 amino acids as referred to above is a peptide derived from the part of a physiological binding partner of IFN-gamma or TNF-α, which is selectively recognized by IFN-gamma or TNF-α. In some embodiments, the synthesis of IFN-gamma or TNF-α can be blocked by si-RNA or small molecule drugs, such as calcineurin inhibitors, phosphodiesterase inhibitors.

According to another aspect of the invention, an inhibitor of CD8+ cells is provided for use in a method for treatment or therapy of delayed fracture healing. In one alternative, such inhibitor of CD8+ cells is a ligand to CD8, selected from the group comprised of an antibody, an antibody fragment, an antibody-like-molecule, an oligopeptide of 6 to 30 amino acids, and a nucleic acid aptamer molecule of 10 to 75 nucleotides in length, and wherein the ligand (the inhibitor) is capable to selectively bind to CD8 with a dissociation constant of $10^{-8}$ mol/l or smaller, and wherein the ligand to CD8 (the inhibitor) is furthermore capable of abrogating or suppressing the biological effects of a CD8+ T cell, particularly capable of inhibiting the secretion IFN-gamma or TNF-α by said CD8+ T cell.

In some embodiments of this aspect of the invention, the inhibitor is a monoclonal antibody raised against CD8. In one embodiment, the inhibitor is a chimeric, humanized or human monoclonal antibody against CD8, including anti-thymocyte globuline.

In one embodiment of this aspect of the invention, the inhibitor is an antibody raised against CD11a/CD18 (LFA-1). In one embodiment of this aspect of the invention, the inhibitor is an antibody raised against CD49d (VLA-4). In one embodiment of this aspect of the invention, the inhibitor is an antibody raised against CD137 (4-1BB).

In one embodiment of this aspect of the invention, the inhibitor is a monoclonal antibody raised against molecules on activated CD8 such as, by way of non-limiting example, CD11a/CD18 (LFA-1), CD49d (VLA-4) or CD137 (4-1BB). In one embodiment, the inhibitor is a chimeric, humanized or human monoclonal antibody. In one embodiment of this aspect of the invention, the inhibitor is a chimeric construct linking an antigen binding-domain selectively binding to CD8 or a CD8– specific activation antigen, such as CD11a/CD18 (LFA-1), CD49d (VLA-4), CD137 (4-1BB), to the Fc-domain of a human immunoglobulin. One example of such construct is the drug alefacept (CAS No. 222535-22-0).

According to yet another aspect of the invention, a pharmaceutical composition for treating delayed fracture healing is provided, comprising an inhibitor of (or ligand to) IFN-gamma or TNF-α or CD8 according to any one of the above aspects of the invention.

In some embodiments, the pharmaceutical composition is formulated for parenteral administration, such as subcutaneous, intravenous, intrahepatic, intramuscular, or local intrafracture administration.

In some embodiments, the pharmaceutical composition comprises from approximately 0.1% to approximately 10% active ingredient. In some embodiments, the pharmaceutical composition comprises from approximately 10% to approximately 100% active ingredient (lyophilisate).

In some embodiments, the pharmaceutical composition comprises an inhibitor of IFN-gamma and an inhibitor of TNF-α. In some embodiments, the pharmaceutical composition comprises an inhibitor of CD8. In some embodiments, the pharmaceutical composition comprises a monoclonal antibody or other neutralizing agents against IFN-gamma and a monoclonal antibody or neutralizing agent (e.g. an Fc-Ig construct directed against TNF-α, such as etanercept) against TNF-α.

According to another aspect of the invention, a dosage form for treating delayed fracture healing is provided, comprising an inhibitor of (or ligand to) IFN-gamma or TNF-α according to any one of the above aspects of the invention.

Dosage forms may be for enteral administration, such as nasal, buccal, rectal, transdermal or oral administration, or as an inhalation form or suppository. Alternatively, parenteral administration may be used, such as subcutaneous, intravenous, intrahepatic or intramuscular injection forms. Optionally, a pharmaceutically acceptable carrier and/or excipient may be present.

Also within the scope of the present invention is a method for treating a patient suffering from delayed fracture healing, comprising the administration of an inhibitor of (or ligand to) IFN-gamma or TNF-α, or a pharmaceutical composition or dosage form according to any one of the above aspects of the invention, to said patient. Similarly, a method for treating a patient suffering from delayed fracture healing, comprising the administration of an agent capable of effecting CD8+ T cell depletion in said patient, such as an antibody to CD8, to said patient, is contemplated.

According to another aspect of the invention, a method for the manufacture of a medicament for treating delayed fracture healing is provided, comprising the use of an inhibitor of (or ligand to) IFN-gamma or TNF-α according to any one of the above aspects of the invention.

Thus, the objects relating to therapeutic application of the invention disclosed herein are:

1. An inhibitor of IFN-gamma (Uniprot P01579) or TNF-α (Uniprot P01375) for use in a method for treatment or therapy of delayed fracture healing, wherein the inhibitor
   a. is a ligand to IFN-gamma or TNF-α capable to selectively bind to IFN-gamma or TNF-α with a dissociation constant of $10^{-8}$ mol/l or smaller, and wherein the inhibitor
   b. is capable of abrogating or suppressing the biological effects of IFN-gamma or TNF-α.
2. The inhibitor of IFN-gamma or TNF-α according to object 1, wherein said inhibitor is selected from the group comprised of an antibody, an antibody fragment, an antibody-like-molecule, a soluble receptor construct, an oligopeptide of 6 to 30 amino acids derived from a receptor to IFN-gamma or TNF-α and a nucleic acid aptamer molecule of 10 to 75 nucleotides in length.
3. An inhibitor of IFN-gamma or TNF-α according to object 1 or 2, wherein said inhibitor is a monoclonal antibody raised against IFN-gamma or TNF-α.
4. An inhibitor of IFN-gamma or TNF-α according to any of the above objects, wherein said inhibitor is a chimeric (partially human), humanized, or human monoclonal antibody.
5. An inhibitor of IFN-gamma or TNF-α according to any of the above objects, wherein said inhibitor is a chimeric construct linking an antigen binding-domain selectively binding to IFN-gamma or TNF-α, to an Fc-domain of a human immunoglobulin.
6. The inhibitor of IFN-gamma or TNF-α according to object 5, wherein the inhibitor is etanercept (CAS No. 185243-69-0).
7. An inhibitor of IFN-gamma or TNF-α for use in a method for treatment of delayed fracture healing, wherein the inhibitor is an inhibitory RNA or DNA molecule targeting mRNA encoding IFN-gamma or TNF-α (si-RNA, mi-RNA, sh-RNA, antisense DNA).
8. An inhibitor of activated CD8+ cells for use in a method for treatment or therapy of delayed fracture healing, wherein said inhibitor is capable to selectively bind to the cell surface of an activated CD8 T cell, and wherein said inhibitor is furthermore capable of abrogating or suppressing the biological effects of an activated CD8+ T cell, particularly capable of inhibiting the secretion IFN-gamma or TNF-α by said CD8+ T cell.
9. An inhibitor of activated CD8+ T cells according to object 8, wherein said inhibitor is a ligand to a member comprised in the CD8 marker group comprising CD8, CD11a/CD18 (LFA-1), CD49d (VLA-4), CD137 (4-1BB), and said inhibitor is capable to selectively bind to said member of said marker group with a dissociation constant of $10^{-8}$ mol/l or smaller.
10. An inhibitor of activated CD8+ T cells according to object 8 or 9, wherein said inhibitor is selected from the group comprised of an antibody, an antibody fragment, an antibody-like-molecule, a soluble receptor construct, an oligopeptide of 6 to 30 amino acids derived from a receptor to IFN-gamma or TNF-α and a nucleic acid aptamer molecule of 10 to 75 nucleotides in length.
11. An inhibitor of activated CD8+ T cells according to any one of object 8 to 10, wherein said inhibitor is a monoclonal antibody raised against CD8, CD11a/CD18 (LFA-1), CD49d (VLA-4) or CD137 (4-1BB).
12. An inhibitor of activated CD8+ T cells according to any one of object 8 to 10, wherein said inhibitor is a chimeric (partially human), humanized, or human monoclonal antibody.
13. The inhibitor of activated CD8+ cells according to object 12, wherein said inhibitor is alefacept (CAS No. 222535-22-0).
14. An inhibitor of activated CD8+ T cells for use in a method for treatment of delayed fracture healing, wherein the inhibitor is an inhibitory RNA or DNA molecule targeting mRNA encoding CD8, CD11a/CD18 (LFA-1), CD49d (VLA-4) or CD137 (4-1BB) (si-RNA, mi-RNA, sh-RNA, antisense DNA).
15. A pharmaceutical composition for treating delayed fracture healing, comprising an inhibitor of IFN-gamma or TNF-α, or an inhibitor of activated CD8 T cells, according to any one of the above objects.
16. The pharmaceutical composition according to object 15, wherein said composition comprises an inhibitor of IFN-gamma and an inhibitor of TNF-α.
17. The pharmaceutical composition according to object 15, wherein said composition comprises an inhibitor of activated CD8 T cells according to any one of objects 8 to 14.
18. A method for treating a patient suffering from delayed fracture healing, comprising administering
   a. an inhibitor of IFN-gamma or TNF-α according to any one of the above objects 1 to 7, or
   b. an inhibitor of activated CD8+ T cells according to any of objects 8 to 14, or
   c. a pharmaceutical composition or dosage form according to any one of the above objects 15 to 17, to said patient.
19. A method for the manufacture of a medicament for treating delayed fracture healing, comprising the use of an inhibitor of IFN-gamma or TNF-α, or of an inhibitor of activated T cells, according to any one of the above objects.

Wherever alternatives for single separable features such as, for example, a marker molecule or an inhibitor are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

Materials and Methods
Subjects and Study Protocol

Between July 2008 and August 2010 15 patients were enrolled with an isolated, closed proximal tibia fracture in this study (aged 23 to 64 years, 9 male and 8 female).

Due to the assessment of biomechanical function and immunological parameters, patients with any chronic diseases (e.g. osteoporosis, diabetes, rheumatoid arthritis, chronic heart failure, renal failure), especially a human immunodeficiency virus infection or hepatitis infection, were excluded from the study. Furthermore, patients with several fractures or with the attendance of the hip joint, shoulder joint or ankle joint were also excluded from the study.

The study was performed in compliance with the International Conference on Harmonisation Guidelines for Good Clinical Practice and the Declaration of Helsinki. All patients gave written informed consent and the study was approved by the Ethics Committee of the Charité—Universitätsmedizin Berlin (Nr. EA1/006/08).

Protocol and Assessment Plan

To assess the early stages in fracture healing and in harmonisation with established clinical examination points during fracture healing, the patients were investigated three-five days post operative (hereafter named "first week"), after two weeks, four weeks, six weeks, twelve weeks and eighteen weeks. At every testing point all patients underwent the following methods.

Blood Samples

On each test day, blood samples were taken in the morning between 9:00 am and 12:00 am after 15 minutes rest in a supine position. All blood samples were immediately moved into a dark, air conditioned room and sent to the laboratory within two hours. Additionally, plasma and serum samples were collected in aliquots and frozen at −80° C.

Full blood count and standard clinical variables (erythrocytes, haemoglobin, hematocrit, thrombocytes, creatinine, sodium, potassium, uric acid, ostase, CRP) were measured in plasma and serum samples according to the laboratory standard operating procedures (SOPs). The serum sample for osteocalcin assessment was immediately centrifuged (3500 rpm/15 minutes), stored in pre-freezed aliquots and sent to the laboratory within three hours.

Cytokines (TNFα, IL-6, total IL-8, IL-10) were measured in plasma samples by using a semiautomatic system. The antibodies and the respective reagents for intracellular cytokine staining were purchased from BD Pharmingen.

T-cell related cluster of differentiation were examined to evaluate the adaptive immunity of the host defense including CD3, CD4, CD8, CD11a+, CD57+ and CD28+. Cell sorting was performed by using BD FACSAria II flow cytometer and the purity of the obtained fractions was determined on the BD LSRII flow cytometer.

CD8+ TEMRA Cells Conditioned Medium for MSC Differentiation

Conditioned media of T cell receptor activated CD8+ TEMRA cells (CD62L-CD45RA+) was obtained from two different donors after informed consent and approval by the local ethics committees on human studies. After depletion of CD62L+ and CD45RO+ cells a positive selection of CD8+ cells from the CD62L-CD45RO− fraction was performed. The CD8+ T cells (1×106 cells/ml DMEM+10% FCS) were stimulated with for 24 hours with CD3CD28CD2 coated beads.

Isolation and Culture of Bone Marrow Derived Mesenchymal Stromal Cells (BM-MSC)

BM-MSCs were isolated from washouts of the femoral bone marrow of five patients (donor age: 39-90 years, mean=73 years; sex: 2 female, 3 male) undergoing hip surgery as described previously. A homogeneous population of BM-MSCs was validated by analysis of the cell surface marker expression using flow cytometric analysis [Glaeser, J. D., S. Geissler, A. Ode, C. J. Schipp, G. Matziolis, W. R. Taylor, P. Knaus, C. Perka, G. N. Duda, and G. Kasper, Modulation of matrix metalloprotease-2 levels by mechanical loading of three-dimensional mesenchymal stem cell constructs: impact on in vitro tube formation. Tissue Eng Part A. 16(10): p. 3139-48 (2010)]. All cell assays described below were performed with BM-MSCs at passages 3-4 from at least 4 different donors in three technical replicates.

Osteogenic Differentiation Assay

Osteogenic differentiation of confluent BM-MSCs was induced by using osteogenic media (OM) supplemented with different concentrations of IFN-γ or TNF-α, respectively. For experiments with CM of ex vivo stimulated sorted CD8+ TEMRA, the CM were diluted 1:2 with double-concentrated OM. The matrix mineralization was visualized with Alizarin Red staining. Quantification was achieved by measuring the absorbance of Alizarin Red (ODAR) after extraction with 10% cetylpyridiniumchloride. Obtained values were normalized to number of viable cells determined by alamarBlue.

BM-MSC Survival and Viability Assay

For the cell viability assay, 2400 BM-MSCs/cm2 were seeded onto 96-well plates one day before the experiment. The next day, medium was exchanged and cells were cultured in EM containing different concentrations of IFN-γ or TNF-α (0, 1, 10 and 100 ng/ml) for three days. Cell viability was measured using alamarBlue cell viability assay. Equal cell seeding were confirmed one day after seeding using CyQuant assay according to manufactures instruction.

BM-MSC Apoptosis Assay

For cell apoptosis assays, 2400 BM-MSCs/cm2 were seeded onto 24 well plates. BM-MSCs were cultured for two days with medium containing the indicated concentration of IFN-γ or TNF-α, respectively. Subsequently, medium was removed and the caspase-3 and -7 activities were measured in cell lysates using Caspase-Glo® 3/7 Assay according to manufactures instructions and values were normalized to cell number determined by CyQuant assay.

Mice Experiments

Mice experiments were performed with 12 week old C57BL/6 mice (n=19) according to the policies and principles established by the Animal Welfare Act, The NIH Guide for Care and Use of Laboratory Animals and the national animal welfare guidelines. CD8+ immune cell depletion in the CD8- T cell group was achieved with an antibody (mCD8 (YTS 169.4), BioXCell) injection (200 μg mCD8, per injection for four consecutive days with the last day being the day of surgery).

CD8+ cell depletion was monitored via FACS analysis (LSR II flow cytometer) using specific antibodies against CD3, CD8a and CD4. The CD8+ T cell group received an intravenous injection in the tail vain of 200 μl with 2.5×106 CD8+ cells on the day before surgery. The osteotomy was performed on the left femur using the MouseExFix system. The femur underwent a μCT analysis (Viva pCT 40) with a voxel size of 10.5 μm, 55 keVp, 145 μA and the volume of interest (VOI) included 2 mm with the osteotomy gap at the centre. The healing outcome at 21d after osteotomy was rated as either bridged or non-bridged by three independent orthopaedic surgeons in a blinded evaluation.

Healing Classification and Data Collection

Every patient underwent several x-ray analyses to assess the stability of the implant and fracture gap during the study time. The examination of the x-rays was performed by three independent, blinded physicians from different directions (orthopaedics, radiologist), to ensure the correct healing outcome and the classification of the patients. Furthermore, functional data (gait analysis) were performed to assess the painless full weight bearing after 12 weeks post operative. To fulfill the definition of a delayed healing process, the patients have to meet one or more of the following criteria.

As established in literature and used in clinics, there are time dependent and radiological criteria for a delayed healing process.

Time Dependent Criteria for Delayed Fracture Healing:

An incomplete fracture healing after 12 post operative weeks based on the callus formation.

Radiological Criteria for Delayed Fracture Healing:

1) An incomplete fracture healing after 12 post operative weeks with a fracture gap of >1 mm.
2) The presence of a resorption zone or incomplete callus formation.
3) An incomplete bridging, which means one to three cortices bridged.
4) No bridging, which means no cortex is bridged.

To quantify the patient's individual post operative situation, the non-union scoring system by Calori was used.

Furthermore, patients' demographic data, ASA classification, main diagnosis, type of operation and implant, concomitant diseases and microbiological data were derived from charts and collected in a database. All patient characteristics are shown in table 1.

TABLE 1

Patient characteristics

| Pat. Nr. | Age | Weight (kg) | Height (cm) | BMI | Smoking | Healing Status |
|---|---|---|---|---|---|---|
| 1 | 47 | 60 | 159 | 23.733 | yes | delayed |
| 2 | 62 | 90 | 183 | 26.874 | no | normal |
| 4 | 57 | 53 | 153 | 22.641 | no | delayed |
| 5 | 39 | 80 | 168 | 28.345 | no | normal |
| 7 | 59 | 62 | 158 | 24.836 | no | delayed |
| 8 | 23 | 75 | 192 | 20.345 | yes | normal |
| 9 | 58 | 97 | 168 | 34.368 | yes | normal |
| 10 | 24 | 60 | 159 | 23.733 | yes | normal |
| 11 | 46 | 80 | 176 | 25.826 | yes | normal |
| 12 | 45 | 92 | 188 | 26.03 | no | delayed |
| 13 | 46 | 86 | 174 | 28.405 | yes | normal |
| 14 | 62 | 66 | 162 | 25.149 | no | delayed |
| 16 | 25 | 90 | 185 | 26.297 | no | normal |
| 17 | 49 | 81 | 172 | 27.38 | yes | delayed |
| 18 | 64 | 70 | 180 | 21.605 | no | delayed |

Gait Analysis

A 3-D-motion analysis was conducted using 12 infrared cameras at a sampling rate of 120 Hz and retro-reflective markers which were attached to the skin on the first and fifth metatarsal head and the heel. Ground reaction forces were collected by two force platforms at 960 Hz.

On each test day the patients performed a walk along a 10 m walkway with self-selected speed. The kinematic data allowed computation of gait parameters such as walking speed, step and stride length, cadence, stride height and the duration of swing and stance phase. Furthermore, the ground reaction forces were taken to compute the peak horizontal force and the stance duration for the affected and the contralateral limb.

The patients also performed a sit to-stand test from a chair with each foot placed on a separate force platform to determine differences in the peak force between the extremities as well as the duration of the sit-to-stand test, reflected by the ground reaction force.

Statistical Analysis

All data are given as mean±standard deviation. The chi-square test was applied to assess the dependency of age and gender between the groups and the Kolmogorov-Smirnov test to determine those values that were not normally distributed. The Mann-Whitney-U test was used for comparison between groups. ANOVA-repeated-measures with Bonferroni correction were applied to scan the variables of each group between the different study time points.

A receiver operation characteristics (ROC-curve) analysis was performed for all differently expressed genes between the two patient groups. For the estimation of positive and negative predictive values, the sensitivity and specificity for each gene derived from the ROC-curve analysis was applied.

All statistical analyses were performed using StatView 4.5 (Abacus Concepts Inc., Berkeley, USA). Statistical significance was indicated at p<0.05.

Each box plot shows median, lower and upper quartile. Significance levels: p<0.05=*/p<0.01=/p<0.0001=*

EXAMPLES

Example 1: Calori Score

Normal and delayed healing patients were similar in age, gender, height and weight. There were no differences in ASA classification, bone quality, bone defect gap, operation technique, number of interventions and smoking status between the groups.

The Calori-Score is calculated by the following factors, wherein the factors are summed up and multiplied by two.

a) Bone factors:

bone quality good (0 Pt), moderate (e.g. mild osteoporotic, 1 Pt), bad (e.g. bone loss, 2 Pt), very bad (e.g. necrotic, avascular 3 Pt.)

primary fracture closed (0 Pt), open 1 degree (1 Pt), open 2-3 degrees A grade (3 Pt), open 3 degrees B-C grade (5 Pt)

additional intervention none (1 Pt), <2 (2 Pt), <4 (3 Pt), >4 (4 Pt)

OP-Invasiveness minimal invasive (e.g. screws, 0 Pt), internal intramedular (e.g. nail, 1 Pt), internal extramedular (2 Pt), osteosynthesis (e.g. bone grafting, 3 Pt)

OP-suitability adequate stability (0 Pt), inadequate stability (1 Pt)

Weber & Cech hypertroph (1 Pt), oligotroph (3 Pt), atroph (5 Pt)

bone-orientation anatomical (0 Pt), non-anatomical (1 Pt)

fracture gap 0.5-1 cm (2 Pt), 1-3 cm (3 Pt), >3 cm (5 Pt)

b) Soft tissue status intact (0 Pt), recent treatment without events (2 Pt), recent treatment of a tissue defect (e.g. multiple incisions, compartment syndrome, 3 Pt), recent complex treatment (4 Pt), bad vascularisation (venous insufficiency, bad capillary filling, 5 Pt), multiple skin lesion or defects (e.g. ulcers, occurrence of implant plates 6 Pt)

c) Patient

ASA grade diabetes 1 degree or 2 degrees (0 Pt), 3 degrees or 4 degrees (1 Pt) no (0 Pt), yes—well adjusted=HbA1c<10 (1 Pt), ja—bad adjusted HbA1c>10 (2 Pt)

blood tests inflammation WCC>12 or ESR>20 or CRP>20 (1 Pt)

infections none (0 Pt), recent infection or suspected infection (1 Pt), septic (4 Pt)

medication steroids (1 Pt), son-steroids (1 Pt)

smoker no (0 Pt), yes (5 Pt).

Delayed healing patients had a higher soft tissue defect with a more complex treatment, a higher clinical infection status and received more steroidal or non steroidal anti inflammatory drugs (table 2).

TABLE 2

| Parameter | Delayed Healing Patients | Normal Healing Patients |
|---|---|---|
| Primary Injury (closed) | 100% (7/7) | 100% (8/8) |
| Fracture Type AO-B | 57.1% (4/7) | 62.5% (5/8) |
| Fracture Type Moore | 42.9% (3/7) | 37.5% (3/8) |
| ASA class one or two | 100% (7/7) | 100% (8/8) |
| Weber & Cech (hypertrophic) | 14.3% (1/7) | 25% (2/8) |
| Weber & Cech (oligotrophic) | 85.7% (6/7) | 75% (6/8) |
| Bone defect gap (0.5-1.0 cm) | 57.1% (4/7) | 75% (6/8) |
| Bone defect gap (1.0-3.0 cm) | 42.9% (3/7) | 25% (2/8) |
| Surgery method (Percutaneous) | 0% (0/7) | 12.5% (1/8) |
| Surgery method (Pin) | 0% (0/7) | 12.5% (1/8) |
| Surgery method (ORIF) | 100% (7/7) | 75% (6/8) |
| Number of interventions (<2) | 85.7% (6/7) | 100% (8/8) |
| Number of interventions (2-4) | 14.3% (1/7) | 0% (0/8) |
| Quality of Bone (good) | 71.4% (5/7) | 87.5% (7/8) |
| Quality of Bone (moderate) | 28.6% (2/7) | 12.5% (1/8) |
| Soft tissue defect (uneventfull surgery) | 14.3% (1/7) | 87.5% (7/8) |
| Soft tissue defect (small treatment) | 28.6% (2/7) | 12.5% (1/8) |
| Soft tissue defect (complex treatment) | 42.9% (3/7) | 0% (0/8) |
| Soft tissue defect (poor vascularity) | 14.3% (1/7) | 0% (0/8) |
| Clinical infection status (clean) | 85.7% (6/7) | 100% (8/8) |
| Clinical infection status (previously infected) | 14.3% (1/7) | 0% (0/8) |
| Steroid/NSAID Therapy | 14.3% (1/7) | 0% (0/8) |
| Smoking status | 25% (1/7) | 37.5% (3/8) |

Figure 1:
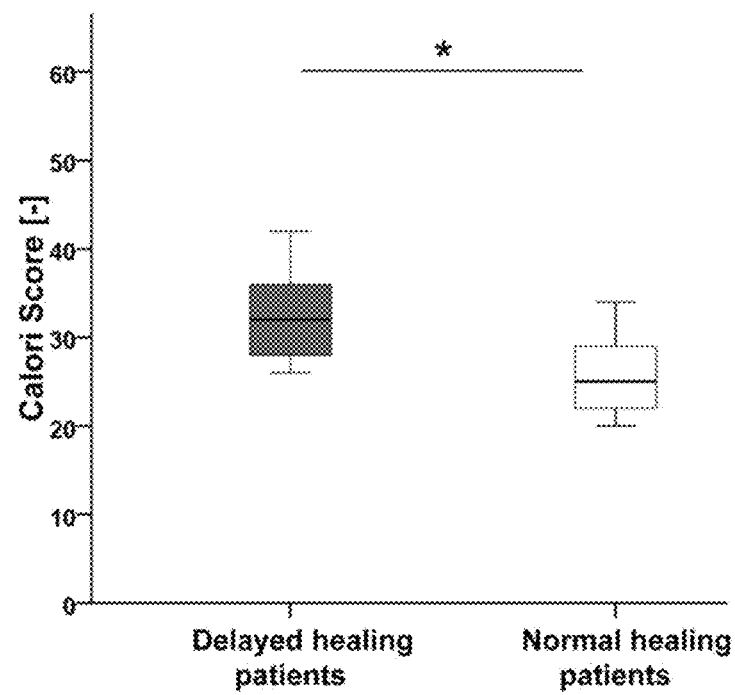
FIG. 1 shows the Calori-Score of normal and delayed healing patients (median, lower and upper quartiles).

FIG. 1 shows the "Calori score", which reflects the risk for post operative healing complications, was significantly higher in the delayed healing patients compared with the normal healing patients (score 32.6±6.3 vs. 25.8±5.1; p=0.05).

Example 2: Gait Analysis

Figure 2A:
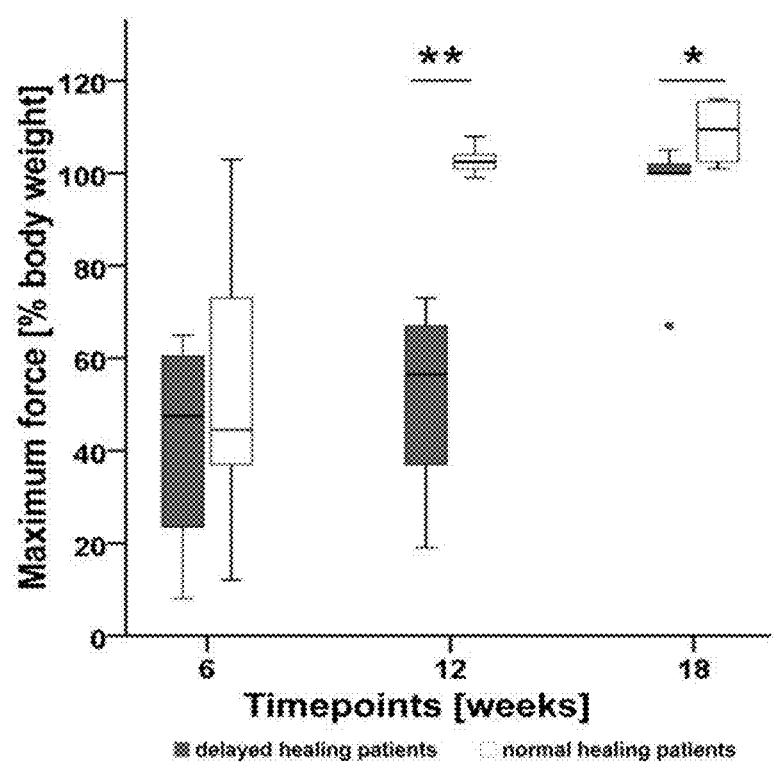
FIGS. 2A and 2B show the maximum ground reaction force (FIG. 2A) and the mean walking speed (FIG. 2B) of normal and delayed healing patients after 6, 12 and 18 weeks post operation (median, lower and upper quartile).
Figure 2B:
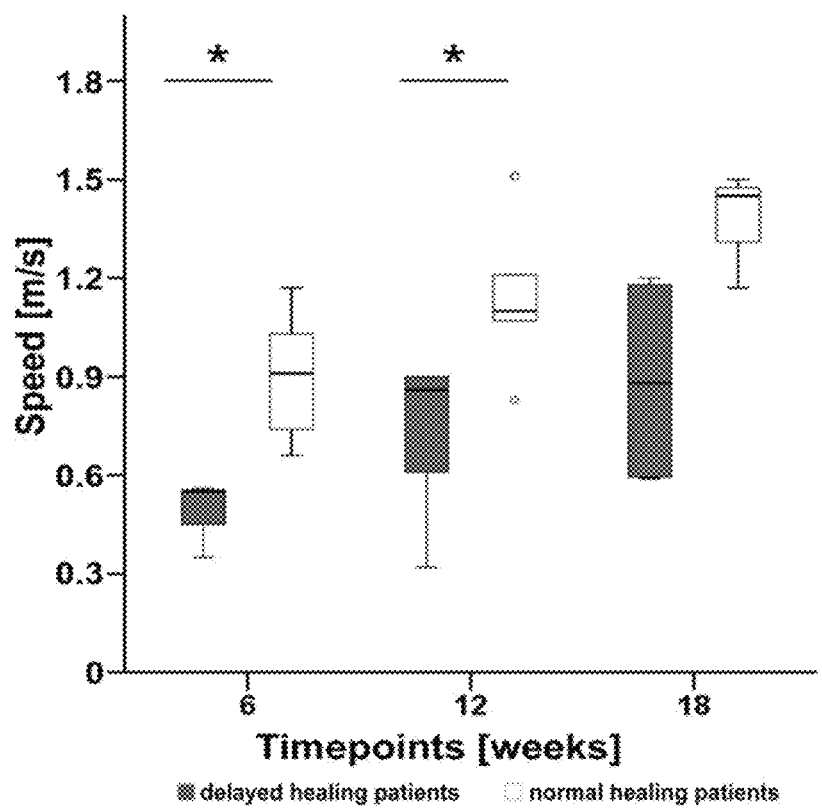

Gait analyses were performed after 6, 12 and 18 weeks post operative to assess the functional status of the patients (FIG. 2). Thereby, delayed healing patients showed a significant lower walking speed and maximum ground reaction force confirming the radiological classification of the two different groups. Furthermore, it clearly shows the prolonged healing time in the delayed healing group. Remarkably, only in week 18 postoperatively, the delayed healing patients meet the walking speed levels of the 6th postoperative week in the normal healing group.

Example 3: Frequency of CD8+/CD4+ Cells in the CD3+ T Cell Population

Figure 3:
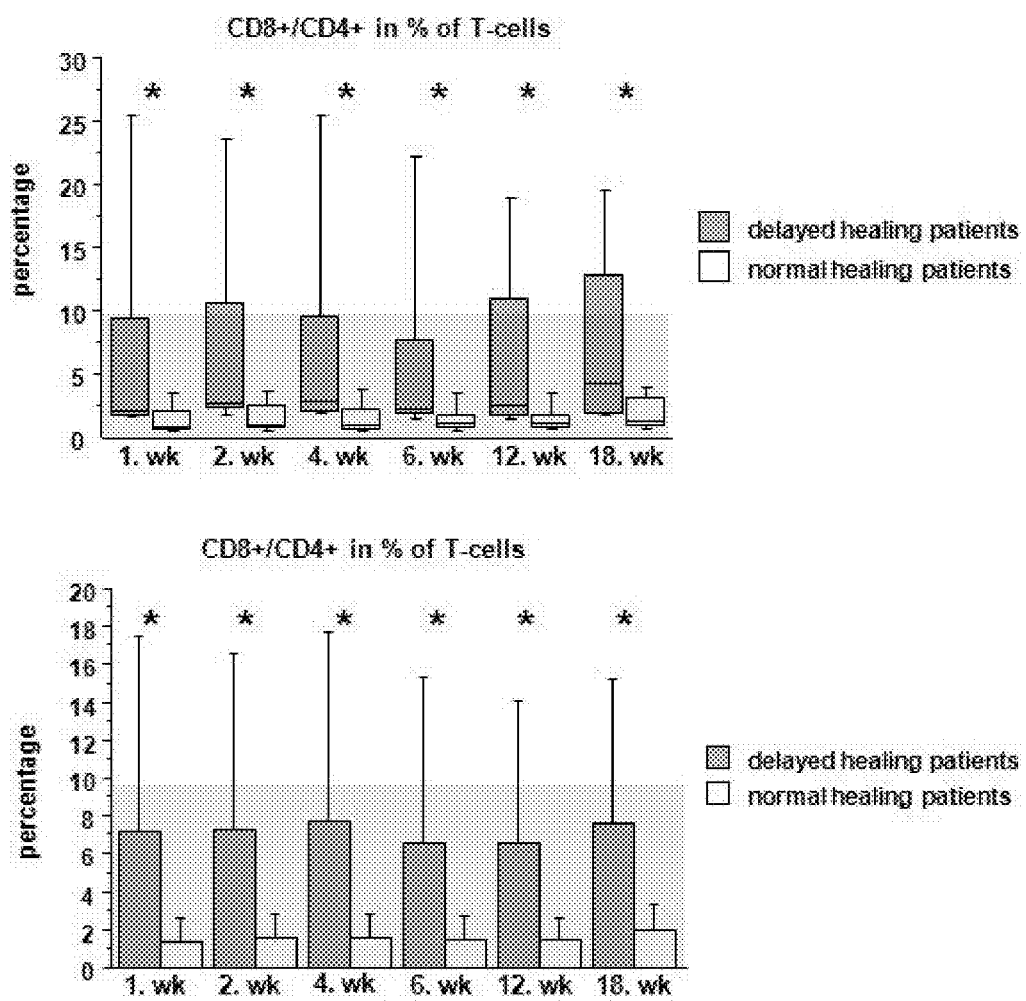
FIG. 3 shows the frequency of CD8+CD4+ cells in the CD3+ T-cell populations of normal and delayed healing patients (upper plot median, lower and upper quartiles, lower plot mean values).

Significant differences for the percentage of CD8+/CD4+ in the CD3+ T-cells were found between the two groups (FIG. 3). Delayed healing patients showed a persistent higher CD8+/CD4+ percentage in the CD3+ T-cells over all time points compared to the normal healing patients. In addition, no changes in the percentage of CD8+/CD4+ of the CD3+ T-cells were observed in both groups over time. Single cell values for each group and time point are shown in table 3.

Example 4: Frequency of CD11a++ Cells in the CD8+ T-Cells Population

Figure 4:
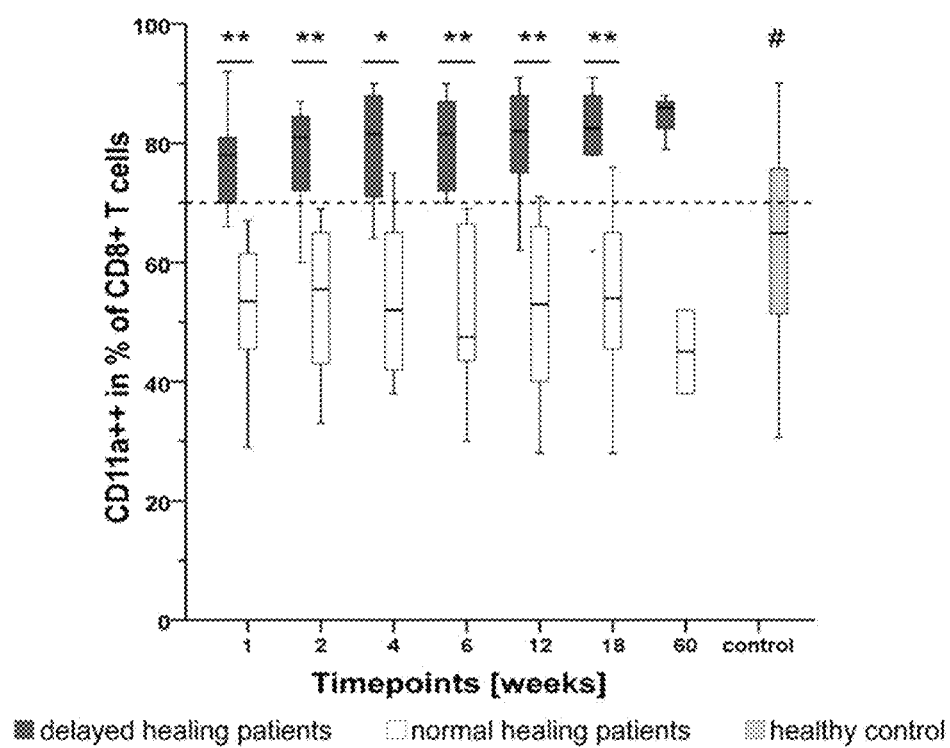
FIG. 4 shows the frequency of CD11a++ cells in the CD8+ T-cell population of normal and delayed healing patients as well as an unfractured healthy control group (median, lower and upper quartiles).

The expression of CD11a++ T-cells in the delayed healing group was significantly higher compared to normal healing patients over the complete study time of 18 weeks. (FIG. 4). Moreover, delayed healing patients showed pathologically enhanced CD11a++ T-cell levels compared to the reference range (dashed line). Furthermore, they showed significantly higher values compared to an unfractured healthy control group. 3 delayed and 3 normal healing patients 60 weeks were assessed after surgery. Both groups showed the same CD11a++ T-cell concentration. No differences were found in each group over time. Single cell values for each group and time point are shown in table 4. An example for two different measurements and analysis of the CD11a++(high positive) and CD11a+(positive) fraction in human patients is shown in FIG. 12.

Example 5: Frequency of CD57+ Cell in the CD8+-T-Cell Population

Figure 5:
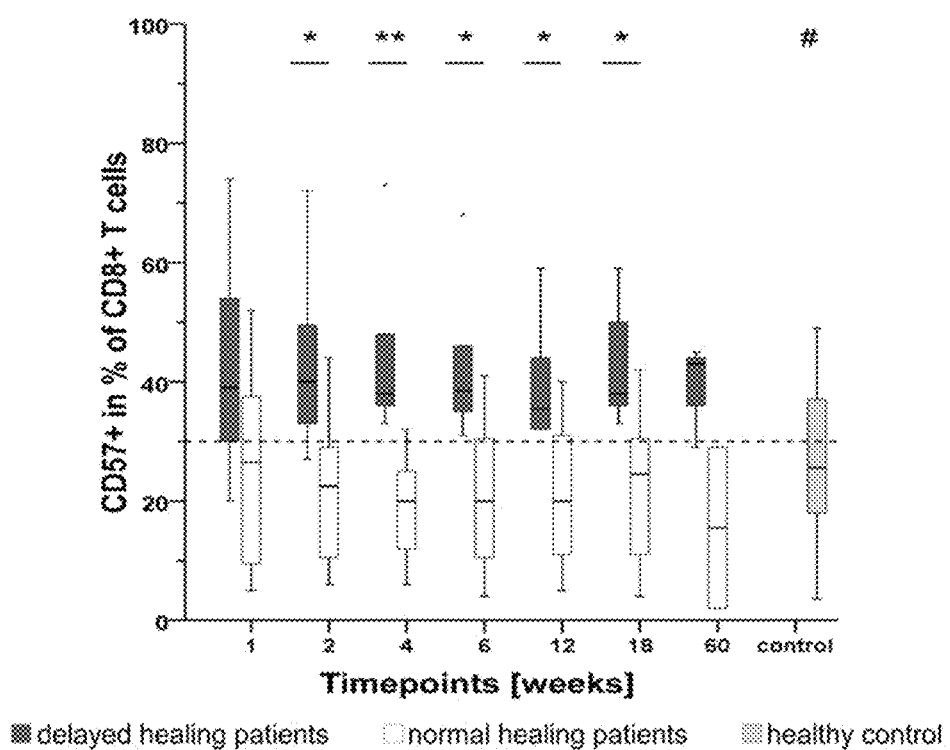
FIG. 5 shows the frequency of CD57+ cells in the CD8+ T-cell population of normal and delayed healing patients as well as an unfractured healthy control group (median, lower and upper quartiles).

Significant differences were observed for the expression of CD57+ in the CD8+ T-cells between delayed healing and normal healing patients (FIG. 5). Remarkably, delayed healing patients showed 55%-73% higher CD57+ percentages compared normal healing patients or the normal values of healthy people. In addition, normal healing patients were well within the reference range, whereas delayed healing patients showed CD8+CD28− levels consequently above this reference range (dashed line). Furthermore, these differences were stable over the complete study time of 18 weeks. Beginning with a slight difference at the first post operative week, these differences became significant during the second week of hospitalization. During the study time, no changes of CD8+CD57+ were found within each group, reflecting rather the individual immune experience than the reaction to the fracture. Single cell values for each group and time point are shown in table 5.

Example 6: Frequency of CD28− Cells in the CD8+-T Cell Population

Figure 6:
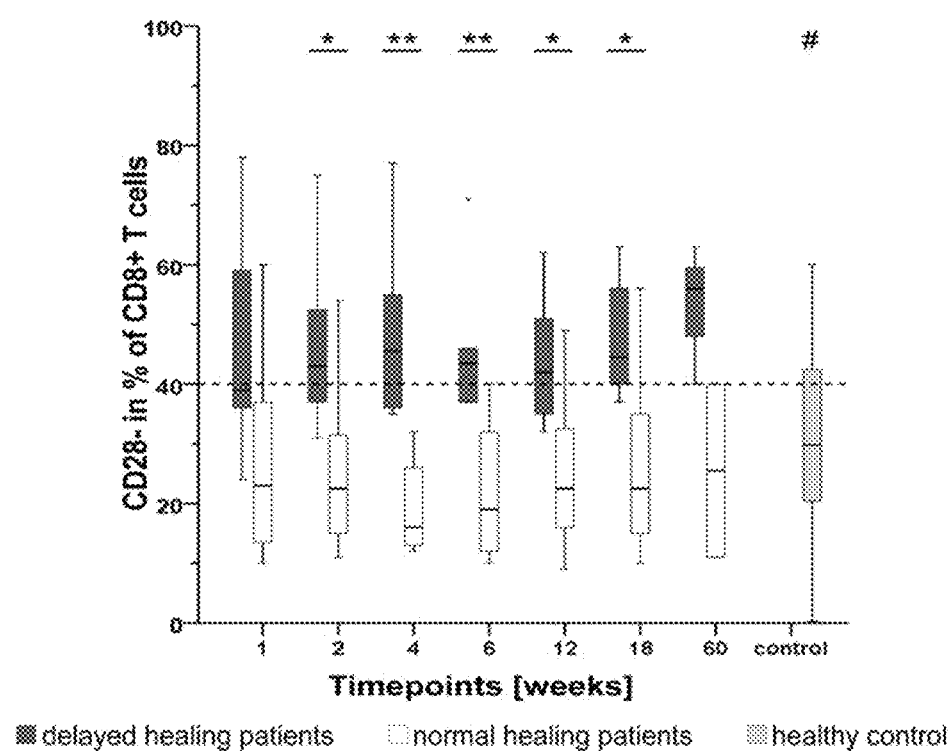
FIG. 6 shows the frequency of CD28− cells in the CD8+ T-cell population of normal and delayed healing patients as well as an unfractured healthy control group (median, lower and upper quartiles).

Similar sequences are shown by the CD8+CD28− T-cells (FIG. 6). Here, delayed healing patients showed persistent higher CD8+CD28− T-cell levels of 29%-34%, compared to normal healing patients or values of healthy people, respectively. Similar to the results of the CD8+CD57+ T-cells, the differences in CD8+CD28− T-cell percentages became significant during the second week of hospitalization and these differences were also stable over the complete study time and 60 weeks after surgery. Furthermore, no significant differences were observed within each group during the study. Single cell values for each group and time point are shown in table 6.

Example 7: Cytokine Expression IL-6, IL-8, TNFα

Figure 7A:
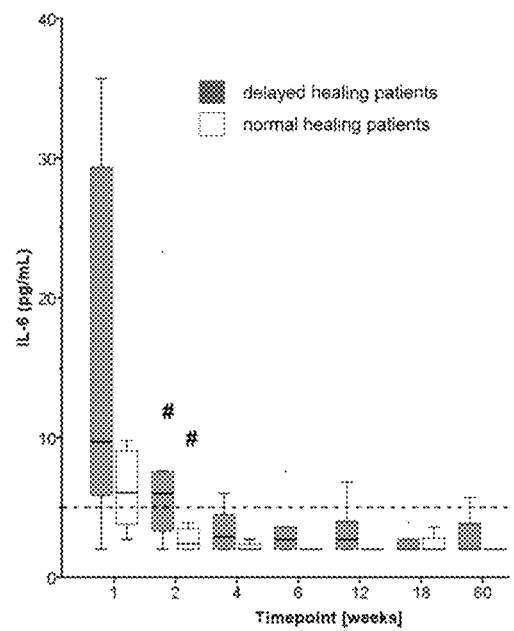
FIGS. 7A and 7B show the cytokine expression (FIG. 7A: IL6.
Figure 7B:
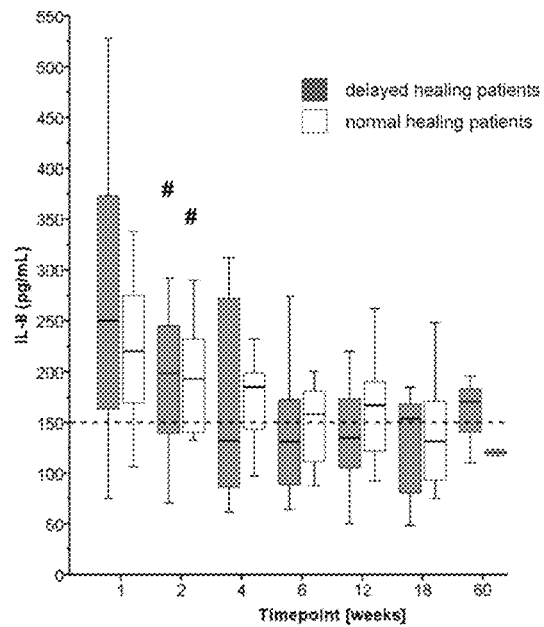

IL-6 levels decreased significantly between the first and second post operative week in both groups (delayed patients p=0.03; normal patients p=0.003) (FIG. 7). However, the IL-6 levels of delayed healing patients after the second postoperative week were still higher, compared to the IL-6 levels of normal healing patients at the first post operative week. Single cell values for each group and time point are shown in table 7.

There were no significant differences in IL-8 levels between the groups, but IL-8 levels decreased significantly from the first to second post operative week in both groups (delayed patients 281.4±162.7 vs. 195.4±77.3 pg/mL; p=0.04 and normal healing patients 219.3±66.8 vs. 182.9±55.9 pg/mL; p=0.01).

For the TNFα levels, no differences between and within both groups over the study time were observed.

Example 8: CD8+ TEMRA Migration from the Peripheral Blood to the Hematoma

Figure 8:
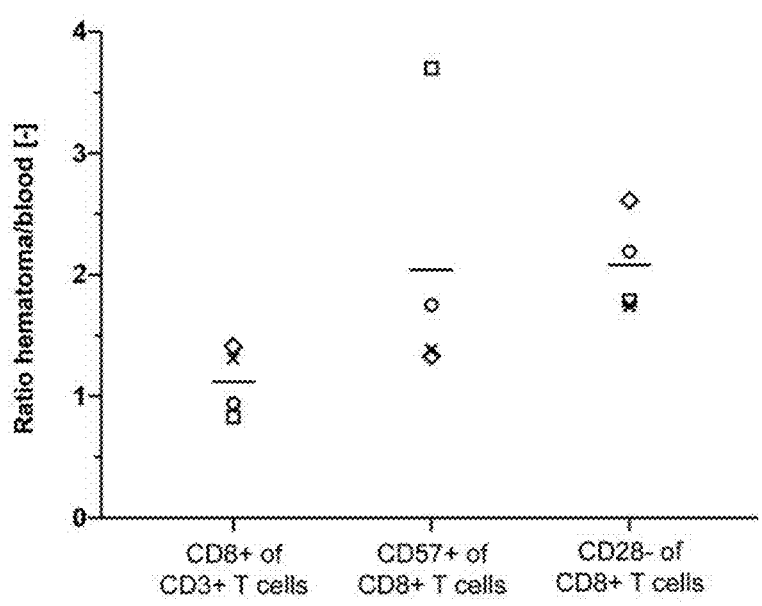
FIG. 8 shows the CD8+ TEMRA migration to the fracture hematoma (ratio).

The fracture hematoma represents the initial phase in fracture healing and therefore could be a key-player for guiding the healing outcome. Thus, it was investigated whether CD8+ TEMRA subset might be enriched at the site of fracture because of their high adhesion molecular expression (e.g. CD11a). Pairs of peripheral blood and fracture hematoma samples of another four patients with a closed proximal tibia fracture were analyzed (FIG. 8). Subset analyses revealed an enrichment of CD28− CD8+ TEMRA in the fracture hematoma from all patients by a factor of 1.8-2.5 (p<0.05) compared to the peripheral blood. Similar results were found for the CD57+CD8+ TEMRA subset, ranging from 1.4 to 3.7-fold enrichment (p=0.07).

Example 9: Strong IFN-γ Production by CD8+ TEMRA Cells

Figure 9:
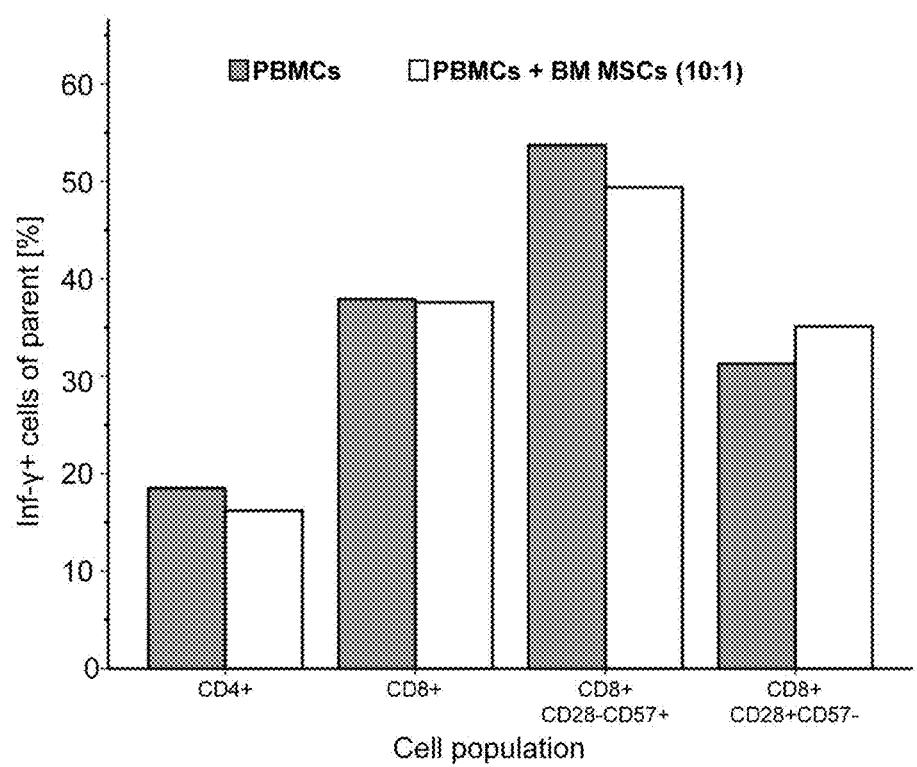
FIG. 9 shows the fraction of IFN-γ producing cells of CD4+ cells, CD8+ cells and CD8+CD57+CD28− cells in peripheral blood mononuclear cells (PBMC) and human bone marrow mesenchymal stromal cells (BM-MSC) (mean value).

CD8+ TEMRA cells are thought to be strong cytokine producers. Indeed, after ex vivo stimulation of T-cells by plate-coated anti-CD3/28 mAb, the strongest cytokine response (>50% IFN-γ producing cells) within the CD3+8+ 57+28− subset was observed compared to other T-cell subsets (CD4+, total CD8+, CD8+57-28+ T-cells; 18-35% IFN-γ producing cells) (FIG. 9). Interestingly, human bone marrow-derived MSC (BM-MSC) that are known to play a key role in bone regeneration and are able to inhibit T-cell proliferation, were not able to suppress IFN-γ secretion by memory T-cells, demonstrating the resistance of those immune cells to negative signals by tissue factors (FIG. 9).

Example 10: Inhibition of the Osteogenesis of Bone Marrow Mesenchymal Stromal Cells by TNF-α and IFN-γ

Next the effect of IFN-γ and TNF-α on bone cells was examined by using in vitro osteogenic differentiation and viability assays.

FIG. 10 shows that (CD3+8+) CD11a++, CD57+ and CD28− T cells inhibit osteogenesis of BM-MSCs via IFN-γ and TNF-α. FIGS. 10 B and C) show representative pictures (upper panel) of BM-MSCs after treatment with osteogenic medium supplemented with indicated IFN-γ and TNF-α concentrations, respectively. Diagrams show optical density values of Alizarin Red ($OD_{AR}$) normalized to cell number. FIGS. 10. D and E) show BM-MSCs vitality determined with alamarBlue® after culture in media supplemented with indicated cytokine concentrations. FIG. 10 F) shows the relative fluorescence value of Caspase-Glo™ 3/7 Assay normalized to total DNA content determined by CyQuant™. FIG. 10 G) shows matrix mineralization of BM-MSCs after cultivation in conditioned media (CM) of ex vivo stimulated sorted CD8+ TEMRA relative to corresponding control without CM. For a-f n=4 and g n=3. Analysis of variance with Bonferroni correction *P<0.05, **P<0.01, #P<0.05 of CM treated cells vs. untreated control. Dashed line indicates the value of untreated control.

Figure 10A:
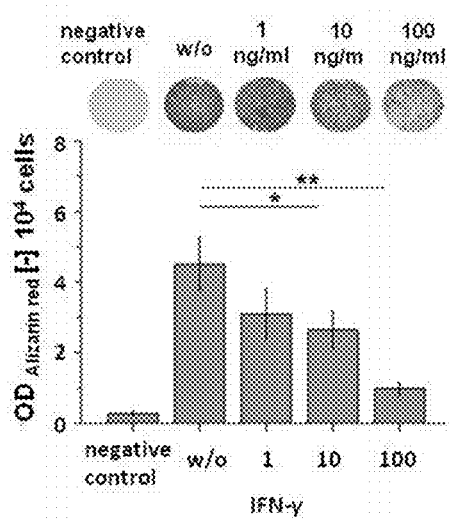
FIGS. 10A-10H show the inhibition of the osteogenesis of bone marrow mesenchymal stromal cells by TNF-α and IFN-γ. The addition of both cytokines inhibited the osteogenic differentiation of human BM-MSCs in concentration-dependent manner (FIG. 10A, IFN-γ and 10B, TNF-α). Effect of TNF-α (FIG. 10D) but not IFN-γ (FIG. 10O) on viability of human BM-MSCs at concentrations of 10-100 ng/ml.
Figure 10B:
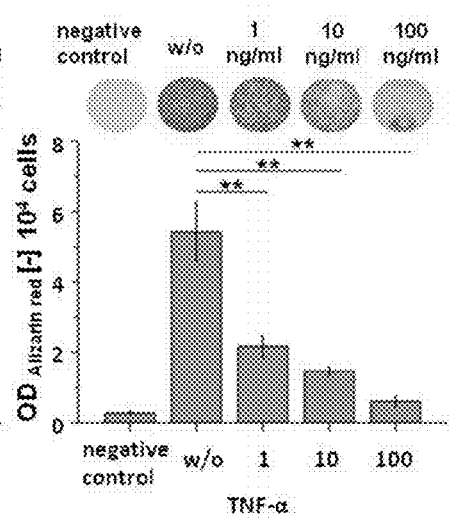
Figure 10C:
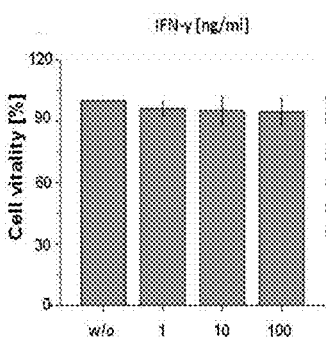
Figure 10D:
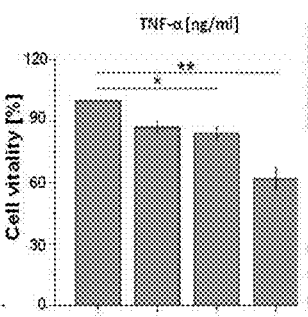
Figure 10E:
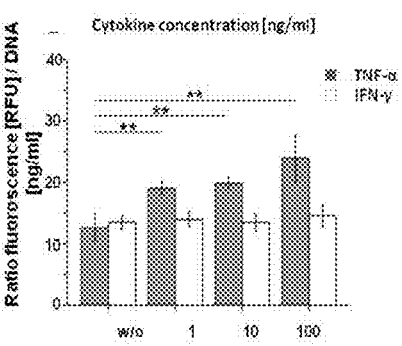

The addition of both cytokines inhibited the osteogenic differentiation of human BM-MSCs in concentration-dependent manner (FIGS. 10A and 10B). Interestingly, TNF-α but not IFN-γ significantly reduced viability of human BM-MSCs at concentrations of 10-100 ng/ml (FIGS. 10C and 10D). To confirm this observation, the apoptosis rate (FIG. 10E) was determined. As expected, TNF-α dose-dependently increased the activity of caspase3/7 in human BM-MSCs, while IFN-γ had no effect.

To further investigate the potential link between the CD8+ TEMRA cells, their specific cytokine secretion and their negative effect on matrix mineralization, conditioned media (CM) of ex vivo stimulated sorted CD8+ TEMRA was used. During osteogenic differentiation, BM-MSCs were cultured in CM, diluted with 1:2 with double-concentrated osteogenic media. Beforehand, the IFN-γ and TNF-α concentrations in CM were determined (Donor 1: $c_{IFN-\gamma}$=1.6 ng/ml, $c_{TNF-\alpha}$=1.8 ng/ml; Donor 2: $c_{IFN-\gamma}$=2.1 ng/ml, $c_{TNF-\alpha}$=5.1 ng/ml) and were found to be clearly increased compared to the CM of unstimulated cells (Donor 2: $c_{IFN-\gamma}$=0.4 ng/ml, $c_{TNF-\alpha}$=0.2 ng/ml).

Figure 10F:
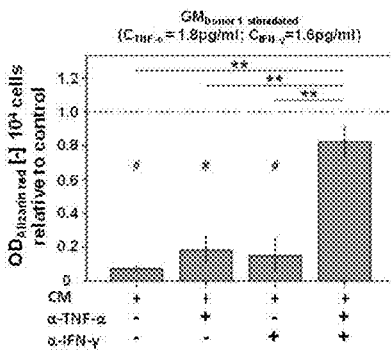
Figure 10G:
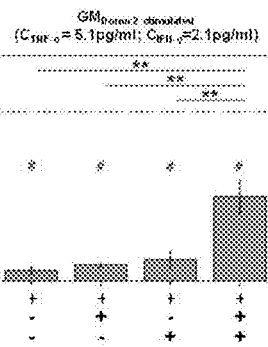
Figure 10H:
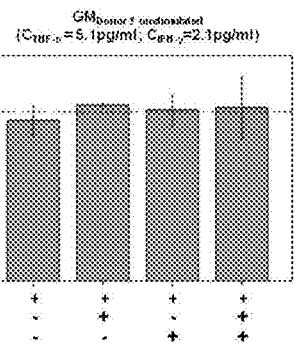

CM from ex vivo stimulated CD8+ TEMRA cells of both donors completely inhibited BM-MSC differentiation while CM from unstimulated CD8+ TEMRA cells showed no significant effect compared to the standard osteogenic media (FIG. 10F-H). Moreover, the addition of neutralizing antibodies either against IFN-γ or TNF-α to the CM of stimulated CD8+ TEMRA cells slightly increased matrix mineralization. The combination of both antibodies, however, almost completely reversed matrix mineralization of BM-MSC.

In summary, these results showed that both IFN-γ and TNF-α are able to inhibit osteogenesis and thereby potentially contribute to the delay in bone healing. The inhibitory effect of TNF-α seems to result from, at least partly, the induction of apoptosis while IFN-γ might directly interfere with osteogenic differentiation.

Example 11: CD8+ Depletion Improves Bone Fracture Healing in a Mouse Model

The potential causal relationship between the enrichment of memory CD8+ T-cells and the pathogenesis of poor bone fracture healing, was further investigated in a mouse model.

FIG. 11 shows that CD8+ depletion in mice improves bone fracture healing wherein A) shows the level of CD8+ of CD3+TCRα/β T-cells in the bone marrow (BM) of CD8+ T cell depleted animals (CD8-, n=6), animals with unaltered immune cell spectrum (WT, n=6), animals housed under semi-sterile conditions (WTexp, n=4) and animals with adaptive transfer of CD8+ T-cells (CD8+, n=3), B) shows the amount of CD62L-CD8+ of CD3+ T cells in the BM of the indicated groups. C and D) show results of quantitative μCT evaluation for the groups described in A, and. E-H) Show representative μCT images for the indicated groups. Analysis of variance with Bonferroni correction *P<0.05, **P<0.01.

In the first animal group, CD8+ cells were depleted by an antibody therapy (CD8- group), which was expected to result in improved bone healing. Successful depletion was confirmed in the blood by flow cytometry. A nearly complete CD8+ T-cell depletion was archived on the day of surgery with a partly recovery over the healing period of 21 days (prior depletion CD3+CD8+20.8%, day of surgery CD3+CD8+0.07%, day 21 CD3+CD8+6.1%). The second group had an unaltered immune cell spectrum (WT-group, n=6) and was raised and kept under specific pathogen free barrier-like housing conditions (SPF). In this group the immune system of the animals had very limited contact to pathogens and therefore only a low percentage of CD62L-CD8+ memory T-cells. In the third group (WT), the mice were housed under semi-sterile conditions without a barrier for at least four weeks. These animals were widely exposed to pathogens, resulting in enhanced CD62L-CD8+ memory T-cells levels. The last group (CD8+) received an adaptive transfer of CD8+ T-cells to further increase the CD8+ T-cell number.

Figure 11A:
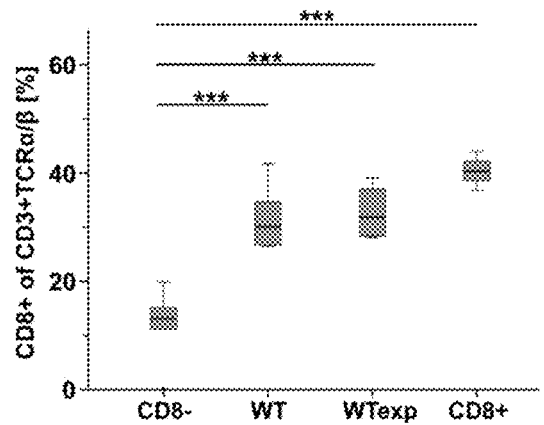
FIGS. 11A-11H show the CD8+ depletion and the improvement of bone fracture healing in a mouse model. The percentage of CD8+T in the CD8− group compared to all other groups (FIG. 11A).
Figure 11B:
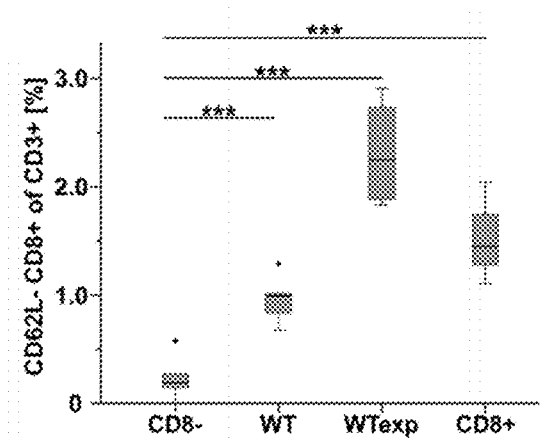
Figure 11C:
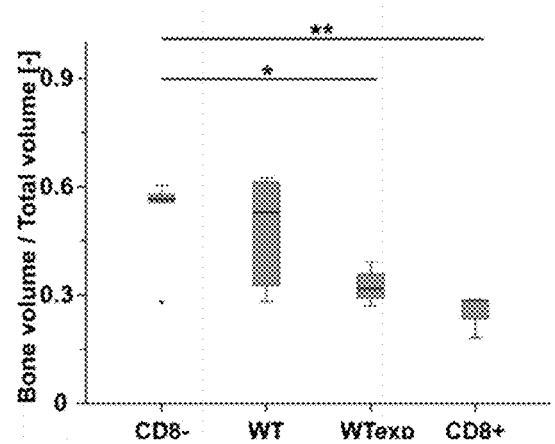
Figure 11D:
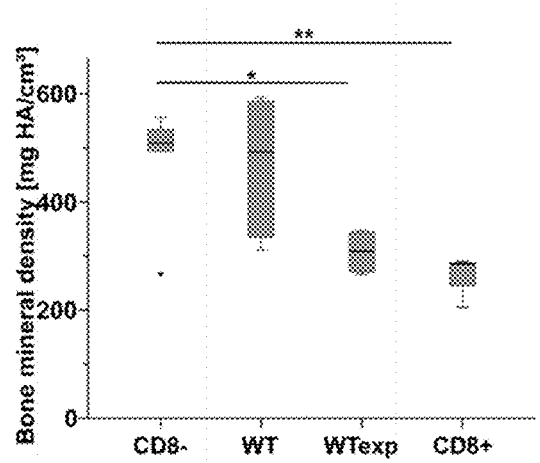
Figure 11E:
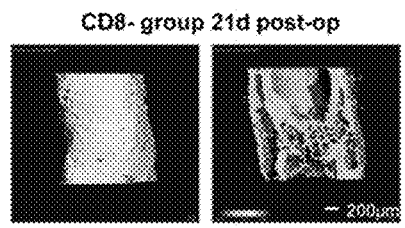
Figure 11F:
Figure 11G:
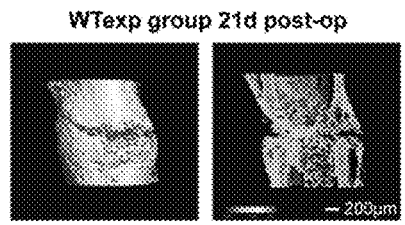
Figure 11H:
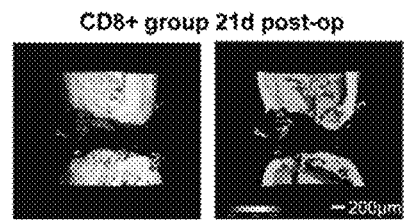

After 21 days post surgery, the amount of the CD8+ T cells in the bone marrow were determined. As expected, the percentage of CD8+ T cells was distinctly lower in the CD8- group compared to all other groups (FIG. 11a). Furthermore, the CD8+ T cells in BM progressively increased from the CD8- group (13±6.6), WT group (30±5.8), WTexp group (37±2.8), to the highest percentages detected in the CD8+ group (40±3.6). Similar results were found for the memory CD62L-CD8+ T cell subpopulation, which were also significantly lower in the CD8- group compared to all other groups (FIG. 11b).

Accordingly, μCT evaluation of the fracture callus quality showed a progressive decrease in the bone volume to total volume ratio (BV/TV) and bone volume density from CD8- group to the CD8+ group (FIG. 11c-h). These results provide evidence for a causal relationship between the enrichment of memory CD8+ T-cells and lower bone quality.

Example 12: CD57+ Cells in the CD8+ T-Cell Population of Bone Fracture Patients in the Blood Before and after Surgery and in the Fracture Hematoma (FH)

Figure 13:
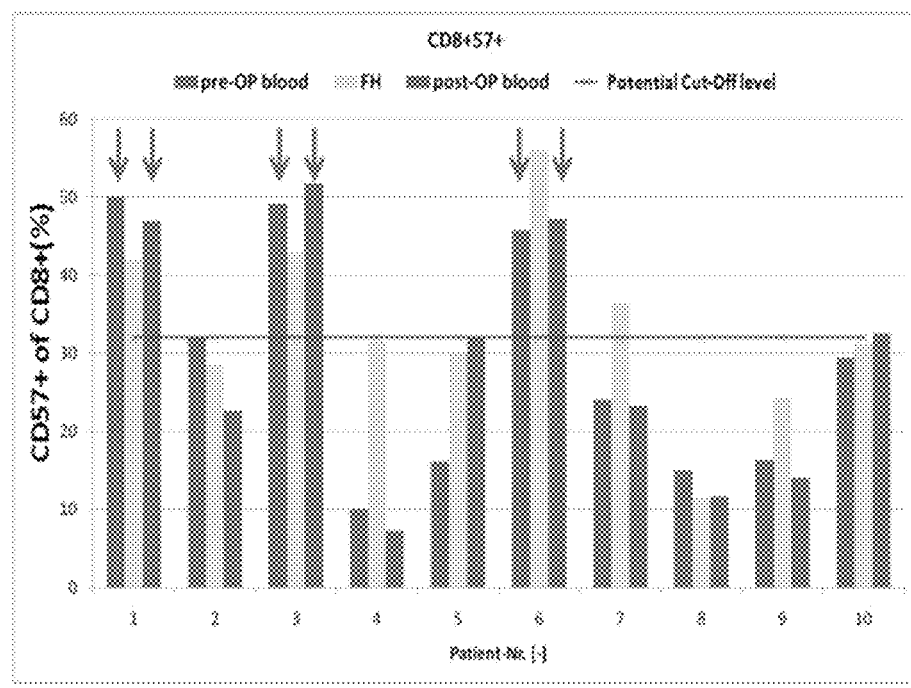
FIG. 13 shows the frequency of CD57+ cells in the CD8+ T-cell population of bone fracture patients in the blood before and after surgery and in the fracture hematoma (FH).

FIG. 13 shows that this cell phenotype is not influenced by the surgery intervention as reflected by similar pre- and postoperative values and therefore suitable as pre-operative prognostic marker. Moreover, using the calculated retrospective cut off value for the prognosis of delayed fracture healing, a delayed healing process can be expected in three of the patients (marked with arrow).

Thus, the frequency of CD8+CD57+ cells in blood and the fracture hematoma is a suitable measure for delayed healing processes in long bone fracture patients.

Example 13: CD28- Cells in the CD8+ T-Cell Population of Bone Fracture Patients in the Blood Before and after Surgery and in the Fracture Hematoma (FH)

Figure 14:
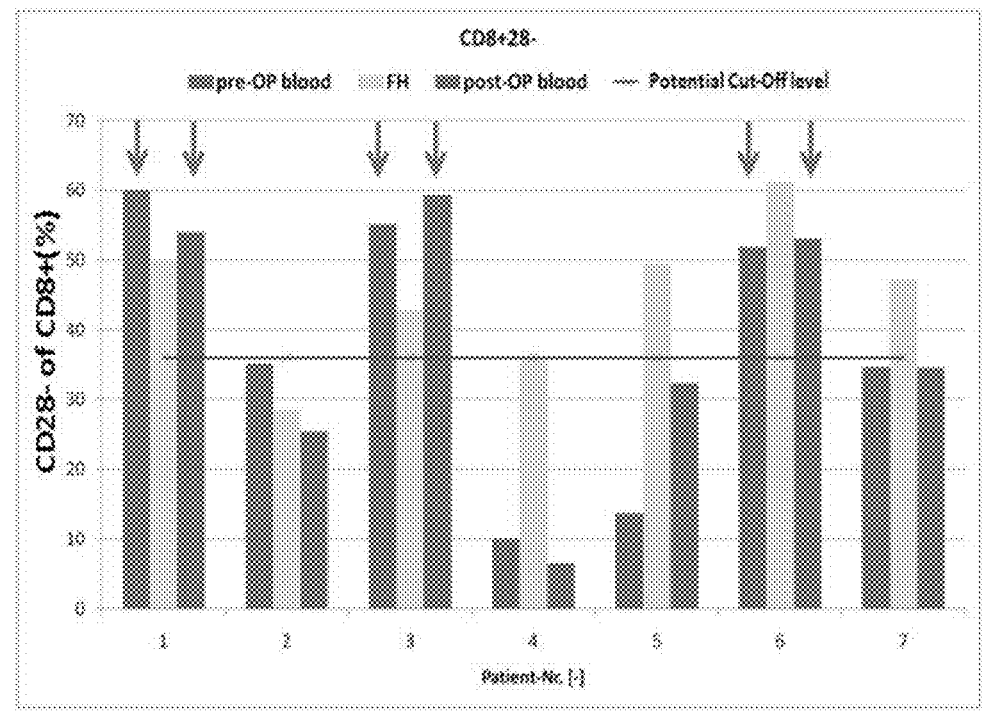
FIG. 14 shows the frequency of CD28− cells in the CD8+ T-cell population of bone fracture patients in the blood before and after surgery and in the fracture hematoma (FH).

Similar results were found for the CD45+3+8+28- T-cells (FIG. 14). Again, this phenotype is not influenced by the surgery intervention and a delayed healing process can be expected in the same three patients as described above.

Example 14: The Frequency of CD57+ Cells and CD28- Cells in the CD4+ T-Cell Population of Bone Fracture Patients in the Blood Before and after Surgery and in the Fracture Hematoma (FH)

Figure 15:
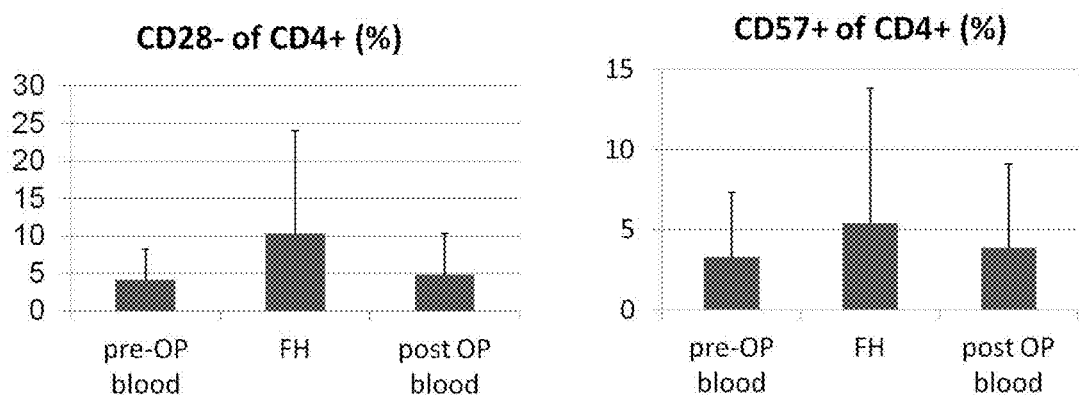
FIG. 15 shows the frequency of CD57+ cells (right panel) and CD28− cells (left panel) in the CD4+ T-cell population of bone fracture patients in the blood before and after surgery and in the fracture hematoma (FH).

The CD8+ TEMRA cells play an important negative role in the fracture healing process. Therefore, the effector/memory and regulatory T-cells (Tregs) t enhances the healing process leading to an earlier and successful healing outcome. FIG. 15 shows that these cells are not influenced by the surgery intervention and found a significant migration into the fracture hematoma.

Concept and Evidence

Delayed or even incomplete (non-union healing) healing of the long bones affects approximately 5-10% of the patients and is associated with poor long-term outcome with a high socio-economic impact. In the present invention 41% of the enrolled patients showed a delayed healing as reflected by fracture gap or callus formation and reduced physical function over 18 weeks after the primary surgery intervention. Remarkably, the walking speed in the 18th postoperative week of the delayed healing patients, were comparable with the levels of the $6^{th}$ postoperative week in the normal healing group.

Most importantly, delayed healing was strongly associated with an amplified and prolonged inflammatory reaction with a significantly enhanced frequency (>2 fold) of terminally differentiated CD8+ effector T-cells expressing the phenotype CD3+8+11a++28-57+(CD8+ TEMRA). This difference was stable over time reflecting rather the individual immune experience than the reaction to the fracture.

CD8+CD57+ expressing lymphocytes are expanded in late stage chronic (viral) infections by dysregulation of the normal apoptotic pathway. Clinical interventions are assumed to play a major role in the patients healing course. In the study present here, no differences in the number of interventions, surgery methods or bone quality between the two groups were found.

Additionally, severe soft tissue defects induced by the injury are commonly known in tibial fractures and may give an additional indication that the patient is high risk one and may benefit from having this risk assessed by the method of the present invention.

Independently from the small patient count the data demonstrates, that the individual immune profile (frequency of CD8+ TEMRA) is a reliable biomarker for predicting outcome of bone fracture healing allowing early interventions.

TABLE 3

(all times given post operation; TC: T-cells)

| Pat. Nr. | CD4+CD8+ TC as % CD3+ TC week 1 | CD4+CD8+ TC as % CD3+ TC week 2 | CD4+CD8+ TC as % CD3+ TC week 4 | CD4+ CD8+ TC as % CD3+ TC week 6 | CD4+ CD8+ TC as % CD3+ TC week 12 | CD4+ CD8+ TC as % CD3+ TC week 18 | CD4+ CD8+ TC as % CD3+ TC month 15 |
|---|---|---|---|---|---|---|---|
| 1  | 3.01  | 2.32  | .     | .     | .     | .     | .     |
| 2  | 0.87  | 0.9   | 0.57  | 0.85  | 0.69  | 3.62  | .     |
| 4  | 0.52  | 0.84  | 0.93  | 1.14  | 0.84  | 1.35  | 1.22  |
| 5  | 0.76  | 0.53  | 0.52  | 1.15  | 1.36  | 1.11  | .     |
| 7  | 1.88  | 2.46  | 3.26  | 2.4   | 2.44  | 4.27  | .     |
| 8  | 0.45  | 0.84  | 1.07  | 0.47  | 0.62  | 0.64  | .     |
| 9  | 0.55  | 0.48  | 0.44  | 0.37  | 0.84  | 0.55  | .     |
| 10 | 0.92  | 1.33  | 2.13  | 1.01  | 1.42  | 0.86  | 1.25  |
| 11 | 4.11  | 4.16  | 4.07  | 4.38  | 3.83  | 4.33  | .     |
| 12 | 1.55  | 1.66  | 1.84  | 1.32  | 1.35  | 1.85  | .     |
| 13 | 2.72  | 3.16  | 3.47  | 2.61  | 2.97  | 3.17  | .     |
| 14 | 11.6  | 13.27 | 9.47  | 7.65  | 8.28  | 10.55 | 11.67 |
| 16 | 0.71  | 1     | 0.6   | 0.86  | 0.83  | 0.94  | 0.56  |
| 17 | 1.62  | 2.79  | 2.24  | 1.84  | 1.89  | 1.78  | .     |
| 18 | 28.96 | 26.12 | 27.19 | 23.77 | 18.94 | 19.56 | 21.26 |

TABLE 4

(all times given post operation; TC: T-cells)

| Pat. Nr. | CD11a+ as % of CD8+ TC week 1 | CD11a+ as % of CD8+ TC week 2 | CD11a+ as % of CD8+ TC week 4 | CD11a+ as % of CD8+ TC week 6 | CD11a+ as % of CD8+ TC week 12 | CD11a+ as % of CD8+ TC week 18 | CD11a+ as % of CD8+ TC month 15 |
|---|---|---|---|---|---|---|---|
| 1  | 66 | 60 | .  | .  | .  | .  | .  |
| 2  | 60 | 69 | .  | 64 | 67 | 76 | .  |
| 4  | 78 | 81 | 84 | 87 | 87 | 91 | 88 |
| 5  | 63 | 64 | 63 | 69 | 71 | 61 | .  |
| 7  | 84 | 85 | 88 | 85 | 91 | 86 | .  |
| 8  | 29 | 33 | 38 | 30 | 28 | 28 | .  |
| 9  | 43 | 62 | 75 | 48 | 57 | 63 | .  |
| 10 | 49 | 40 | 38 | 45 | 36 | 46 | 38 |
| 11 | 67 | 66 | 67 | 69 | 65 | 67 | .  |
| 12 | 66 | 68 | 64 | 72 | 62 | 62 | .  |
| 13 | 48 | 46 | 46 | 42 | 44 | 47 | .  |
| 14 | 78 | 84 | 79 | 70 | 75 | 79 | 79 |
| 16 | 58 | 49 | 52 | 47 | 49 | 45 | 52 |
| 17 | 74 | 76 | 71 | 78 | 77 | 78 | .  |
| 18 | 92 | 87 | 90 | 90 | 88 | 88 | 86 |

TABLE 5

(all times given post operation; TC: T-cells)

| Pat. Nr. | CD57+ as % of CD8+ TC week 1 | CD57+ as % of CD8+ TC week 2 | CD57+ as % of CD8+ TC week 4 | CD57+ as % of CD8+ TC week 6 | CD57+ as % of CD8+ TC week 12 | CD57+ as % of CD8+ TC week 18 | CD57+ as % of CD8+ TC month 15 |
|---|---|---|---|---|---|---|---|
| 1 | 56 | 48 | . | . | . | . | . |
| 2 | 52 | 44 | . | 32 | 40 | 42 | . |
| 4 | 20 | 27 | 38 | 31 | 35 | 39 | 29 |
| 5 | 30 | 30 | 29 | 41 | 30 | 30 | . |
| 7 | 24 | 28 | 33 | 35 | 32 | 33 | . |
| 8 | 7 | 8 | 6 | 4 | 5 | 4 | . |
| 9 | 12 | 13 | 18 | 18 | 17 | 16 | . |
| 10 | 5 | 6 | 6 | 5 | 6 | 6 | 2 |
| 11 | 23 | 22 | 21 | 16 | 16 | 22 | . |
| 12 | 39 | 38 | 38 | 46 | 32 | 36 | . |
| 13 | 36 | 23 | 20 | 22 | 23 | 27 | . |
| 14 | 52 | 51 | 48 | 40 | 44 | 50 | 43 |
| 16 | 39 | 28 | 32 | 29 | 32 | 31 | 29 |
| 17 | 36 | 40 | 36 | 37 | 36 | 37 | . |
| 18 | 74 | 72 | 73 | 68 | 59 | 59 | 45 |

TABLE 6

(all times given post operation; TC: T-cells)

| Pat. Nr. | CD28− in % of CD8+ TC week 1 | CD28− in % of CD8+ TC week 2 | CD28− in % of CD8+ TC week 4 | CD28− in % of CD8+ TC week 6 | CD28− in % of CD8+ TC week 12 | CD28− in % of CD8+ TC week 18 | CD28− in % of CD8+ TC month 15 |
|---|---|---|---|---|---|---|---|
| 1 | 59 | 49 | | | | | |
| 2 | 60 | 54 | | 40 | 49 | 56 | |
| 4 | 24 | 34 | 55 | 41 | 46 | 49 | 40 |
| 5 | 34 | 34 | 32 | 34 | 33 | 35 | |
| 7 | 33 | 31 | 35 | 37 | 35 | 40 | |
| 8 | 10 | 11 | 12 | 10 | 9 | 10 | |
| 9 | 11 | 14 | 14 | 18 | 16 | 16 | |
| 10 | 16 | 16 | 16 | 12 | 19 | 14 | 11 |
| 11 | 17 | 20 | 12 | 12 | 16 | 17 | |
| 12 | 39 | 43 | 41 | 46 | 32 | 40 | |
| 13 | 29 | 25 | 20 | 20 | 26 | 28 | |
| 14 | 59 | 56 | 50 | 46 | 51 | 56 | 56 |
| 16 | 40 | 29 | 32 | 30 | 32 | 35 | 40 |
| 17 | 39 | 40 | 36 | 37 | 38 | 37 | |
| 18 | 78 | 75 | 77 | 71 | 62 | 63 | 63 |

TABLE 7

(all times given post operation)

| Pat. Nr. | IL-6 in pg/ml week 1 | IL-6 in pg/ml week 2 | IL-6 in pg/ml week 4 | IL-6 in pg/ml week 6 | IL-6 in pg/ml week 12 | IL-6 in pg/ml week 18 | IL-6 in pg/ml month 15 |
|---|---|---|---|---|---|---|---|
| 1 | 31.2 | 7.6 | | | | | |
| 2 | 4.8 | 3.9 | 2 | 2 | 2 | 3.6 | |
| 4 | 5.4 | 2 | 2 | 2.2 | 2 | 2 | 2 |
| 5 | 7.3 | 2 | 2 | 2 | 2 | 2 | |
| 7 | 6.3 | 6 | 6 | 7.6 | 6.8 | 4 | |
| 8 | 9.3 | 2 | 2 | 2 | 2 | 2 | |
| 9 | 9.8 | 6.3 | 2.7 | 4.4 | 3.5 | 6.5 | |
| 10 | 3.8 | 3 | 2 | 2 | 2 | 2 | 2 |
| 11 | 3.8 | 2 | 2 | 2 | 2 | 2 | |
| 12 | 27.5 | 23.2 | 3.3 | 2 | 4 | 2 | |
| 13 | 2.7 | 2 | 2 | 2 | 2 | 2 | |
| 14 | 2 | 2 | 2 | 2 | 2 | 2 | 2 |
| 16 | 8.8 | 2.8 | 4.2 | 2 | 2 | 2 | 2 |
| 17 | 9.7 | 7.5 | 4.5 | 3.6 | 2.7 | 2 | |
| 18 | 35.7 | 4.6 | 2.5 | 3.2 | 2.7 | 2.7 | 5.7 |

We claim:

1. A method for treatment of delayed bone fracture healing, comprising:
    (a) obtaining a blood sample from a subject having a fracture and undergoing a primary surgical intervention to repair the fracture, wherein the blood sample is obtained pre-surgery and/or within 14 days from surgery;
    (b) performing a flow cytometry assay comprising determining the frequency of a subpopulation of CD8+ cells selected from the group consisting of cells that are CD8+CD57+, CD8+CD28−, and CD8+CD28−CD57+, in the blood sample obtained from the subject;
    (c) identifying the subject as having an elevated probability for delayed fracture healing within 18 weeks post-surgery when the frequency of the subpopulation cells that are CD28− CD57+ or CD57+ is at least 30% of the CD8+ cells in the blood sample, wherein delayed fracture healing comprises reduced physical function as compared to normal healing; and
    (d) treating the identified subject of (c) by administering a medicament for treating delayed fracture healing selected from the group consisting of a steroidal anti-inflammatory drug, a non-steroidal anti-inflammatory drug, and alefacept having CAS No. 222535-22-0.

2. The method according to claim 1, further comprising determining a Calori-Score of said subject.

\* \* \* \* \*